(12) United States Patent
Vennerstrom et al.

US007371778B2

(10) Patent No.: US 7,371,778 B2
(45) Date of Patent: *May 13, 2008

(54) SPIRO AND DISPIRO 1,2,4-TRIOXOLANE ANTIMALARIALS

(75) Inventors: Jonathan L. Vennerstrom, Omaha, NE (US); Yuxiang Dong, Omaha, NE (US); Jacques Chollet, Basel (CH); Hugues Matile, Basel (CH); Xiaofang Wang, Omaha, NE (US); Kamaraj Spiraghavan, Omaha, NE (US); William N. Chapman, Parkville (AU)

(73) Assignee: Medicines for Malaria Venture MMV (CH)

(*) Notice: Subject to any disclaimer, the term of this patent is extended or adjusted under 35 U.S.C. 154(b) by 323 days.

This patent is subject to a terminal disclaimer.

(21) Appl. No.: 11/121,451

(22) Filed: May 4, 2005

(65) Prior Publication Data

US 2005/0256185 A1 Nov. 17, 2005

Related U.S. Application Data

(63) Continuation-in-part of application No. 10/742,010, filed on Dec. 19, 2003, now Pat. No. 6,906,205, which is a continuation-in-part of application No. PCT/US02/19767, filed on Jun. 21, 2002.

(51) Int. Cl.
*A61K 31/357* (2006.01)
*C07D 323/02* (2006.01)
(52) U.S. Cl. ..................... 514/462; 549/336
(58) Field of Classification Search ............... 549/341, 549/336; 514/462
See application file for complete search history.

(56) References Cited

U.S. PATENT DOCUMENTS

| | | | |
|---|---|---|---|
| 3,621,062 A | 11/1971 | Archer et al. | |
| 3,673,222 A | 6/1972 | Archer et al. | |
| 3,682,991 A | 8/1972 | Tullar et al. | |
| 4,816,478 A | 3/1989 | Thornfeldt | |
| 4,978,676 A | 12/1990 | Thornfeldt | |
| 5,053,342 A | 10/1991 | Lawrence | |
| 5,171,676 A | 12/1992 | Zitter et al. | |
| 5,216,175 A | 6/1993 | Avery et al. | |
| 5,219,880 A | 6/1993 | Thornfeldt | |
| 5,270,344 A | 12/1993 | Herman | |
| 5,430,148 A | 7/1995 | Webber et al. | |
| 5,510,356 A | 4/1996 | Vennerstrom | |
| 5,559,145 A | 9/1996 | Jeffort | |
| 5,578,637 A | 11/1996 | Lal et al. | |
| 5,614,178 A | 3/1997 | Bloom et al. | |
| 5,672,624 A | 9/1997 | Posner | |
| 5,721,209 A | 2/1998 | Horwitz et al. | |
| 5,780,675 A | 7/1998 | Royer et al. | |
| 5,817,692 A | 10/1998 | Posner | |
| 5,932,591 A | 8/1999 | Posner et al. | |
| 6,486,199 B1 * | 11/2002 | Vennerstrom et al. | 514/462 |
| 6,825,230 B2 * | 11/2004 | Vennerstrom et al. | 514/462 |
| 6,906,205 B2 | 6/2005 | Vennerstrom | |

OTHER PUBLICATIONS

Stephen M. Bebge, Lyle D. Bighley and Donald C. Monkhouse "Pharmaceutical Salts" Journal of Pharmaceutical Sciences, 1977, 66, 1-19.*
Wolff, Manfred E. "Burger's Medicinal Chemistry, 5ed, Part I", John Wiley & Sons, 1995, pp. 975-977.*
Banker, G.S. et al, "Modern Pharmaceutics, 3ed.", Marcel Dekker, New York, 1996, pp. 451 and 596.*
Carlos Franco-Paredes, José Ignacio Santos-Preciado "Problem pathogens: prevention of malaria in travelers" Lancet Infectuous Diseases 2006, 6, 139-49.*
Posner, "Antimalarial peroxides in the qinghaosu (artemisinin) and yingzhaosu families", *Exp. Opin. Ther. Patents* 8(11) 1487-1493 (1998) Ashley Publications Ltd. ISSN 1354-3776.
Jefford, "Peroxidic Antimalarials", *Advances in Drug Research*, vol. 29:271-323 (ISBN 0-12-013329-6) copyright 1997 Academic Press Ltd.
De Almeida Barbosa, Luiz-Claudio, "The design, synthesis and biological evaluation of stable ozonides with antimalarial activity", *J. Chem. Soc., Perkin Trans. 1*, 1101-1105 (1996).
De Almeida Barbosa, Luiz-Claudio, "Synthesis of some Stable Ozonides with Anti-malarial Activity", *J. Chem. Soc., Perkin Trans. 1*, 3251 (1992).
Vennerstrom, et al., "Dispiro-1,2,4,5-tetraoxanes: A New Class of Antimalarial Peroxides", *J. Med. Chem.* 35(16):3023-3027 (1992).
Kuel, Helmut: "Uber Konstitution und Entstehung der Ozonide von Bis-adamantyliden und Bis-Blcyclo '3.3.1lnon-9-yliden" *Chemische Berichte*, vol. 108, No. 4, 1975, pp. 1207-1217, XP002217805.
Tabuchi, T: "Ozonolysis of vinyl ethers in the presence of α-diketones and α-keto esters", *J. Org. Chem.*, vol. 56, 1991, pp. 6591-6595, XP001117555.
Dussault, P.J.: "Selectivity in Lewis acid-medlated fragmentations of peroxides and ozonides; application to the synthesis of alkenes, homoallylethers, and 1,2-dioxolanes", *Perkin Trans*, vol. 1, 2000, pp. 3006-3013, XP001117556.
Griesbaum, Karl, "Diozonides from Coozonolyses of Suitable O-Methyl Oximes and Ketones", *Tetrahedron*, Elsevier Science Publishers, Amsterdam, NL, vol. 53, No. 15, Apr. 14, 1997, pp. 5463-5470 XP004105588.
Meshnick, S:"Artemisinin and the Antimalarial Endoperoxides: From Herbal Remedy to Targeted Chemotherapy", *Microbiological Reviews*, American Society for Microbiology, Washington, DC, US, vol. 60, No. 2, Jun. 1, 1996, pp. 301-315, XP002052313.

* cited by examiner

*Primary Examiner*—Rita Desai
*Assistant Examiner*—David K O'Dell
(74) *Attorney, Agent, or Firm*—McKee, Voorhees & Sease, P.L.C.

(57) ABSTRACT

A means and method for treating malaria, schistosomiasis, and cancer using a spiro or dispiro 1,2,4-trioxolane is described. The preferred 1,2,4-trioxolanes include a spiroadamantane group on one side of the trioxolane group, and a spirocyclohexyl on the other side of the trioxolane group, whereby the spirocyclohexyl ring is preferably substituted at the 4-position. In comparison to artemisinin semisynthetic derivatives, the compounds of this invention are structurally simple, easy to synthesize, non-toxic, and potent against malarial parasites.

11 Claims, No Drawings

SPIRO AND DISPIRO 1,2,4-TRIOXOLANE ANTIMALARIALS

CROSS REFERENCE TO RELATED APPLICATION

The present invention is a continuation-in-part of U.S. Ser. No. 10/742,010 filed Dec. 19, 2003, now U.S. Pat. No. 6,906,205 which was a continuation-in-part of PCT/US02/19767 filed Jun. 21, 2002, the disclosures of which are herein specifically incorporated by reference.

FIELD OF THE INVENTION

This invention relates to compositions and methods for treating malaria. Specifically, this invention relates to pharmaceutical compositions including spiro and dispiro trioxolanes, and methods of their use and manufacture.

BACKGROUND OF THE INVENTION

Malaria is an acute and often chronic infectious disease resulting from the presence of protozoan parasites within red blood cells. Caused by single-celled parasites of the genus *Plasmodium*, malaria is transmitted from person to person by the bite of female mosquitos.

Although once prevalent in North America and other temperate regions of the world, today malaria occurs mostly in tropical and subtropic countries. Each year, between 400 million and 600 million people contract the disease, and 1.5 million to 2.7 million die of the disease.

Four species of *Plasmodium* protozoan parasites are generally responsible for malaria, including *Plasmodium vivax, Plasmodium falciparum, Plasmodium malariae*, and *Plasmodium ovale*. Of the four, *Plasmodium falciparum* is the most dangerous, accounting for half of all clinical cases of malaria and 90% of deaths from the disease.

The transmission of malaria begins when a female mosquito bites a human already infected with the malaria parasite. When the infected mosquito bites another human, sporozoites in the mosquito's saliva are transferred into the blood, which then travel to the liver. In the liver, the sporozoites divide rapidly, then enter the bloodstream where they invade red blood cells. Inside these blood cells, the merozoites multiply rapidly until they cause the red blood cells to burst, releasing into the blood stream a new generation of merozoites that then infect other red blood cells.

The symptoms associated with malaria are generally associated with the bursting of the red blood cells. The destruction of the red blood cells spills wastes, toxin, and other debris into the blood. This in turn causes an intense fever that can leave the infected individual exhausted and bedridden. More severe symptoms associated with repeat infections and/or infection by *Plasmodium falciparum* include anemia, severe headaches, convulsions, delirium and, in some instances, death.

The treatment of malaria has been especially difficult due to the ability of malaria parasites to develop resistance to drugs. Quinine, an antimalarial compound that is extracted from the bark of the South American cinchona tree, is one of the oldest and most effective pharmaceuticals in existence. The downside to quinine is that it is short-acting, and fails to prevent disease relapses. Further, quinine is associated with side effects ranging from dizziness to deafness.

Chloroquine is a synthetic chemical similar to quinine. It became the drug of choice for malaria when it was developed in the 1940s due to its effectiveness, ease of manufacture, and general lack of side effects. However, in the last few decades, malaria parasites in many areas of the world have become resistant to chloroquine.

Mefloquine is another synthetic analog of quinine that has been used in the treatment of malaria. Malaria parasites have also developed resistance to mefloquine, however. Mefloquine is also associated with undesirable central nervous side effects in some patients, including hallucinations and vivid nightmares.

Antifolate drugs are effective against malaria parasites by inhibiting their reproduction. Although the parasites have also developed a resistance to antifolate drugs, the drugs can still be used effectively in combination with other types of antimalarials. The use of combination therapies in treating malaria has the drawbacks of being inconvenient and expensive, however.

More recent developments in the treatment of malaria have involved the use of the peroxide functional group, as exemplified by the drug artemisinin, which contains a unique 1,2,4-trioxane heterocyclic pharmacophore. The antimalarial action of artemisinin is due to its reaction with the iron in free heme molecules in the malaria parasite with the generation of free radicals leading to cellular destruction.

The discovery of artemisinin (qinghaosu), a naturally occurring endoperoxide sesquiterpene lactone (Meshnick et al., 1996; Vroman et al. 1999; Dhingra et al., 2000) initiated a substantial effort to elucidate its molecular mechanism of action (Jefford, 1997; Cumming et al., 1997) and to identify novel antimalarial peroxides (Dong and Vennerstrom, 2001). Many synthetic 1,2,4-trioxanes, 1,2,4,5-tetraoxanes, and other endoperoxides have been prepared.

Although the clinically useful semisynthetic artemisinin derivatives are rapid acting and potent antimalarial drugs, they have several disadvantages including recrudescence, neurotoxicity, (Wesche et al., 1994) and metabolic instability. (White, 1994). A fair number of these compounds are quite active in vitro, but most suffer from low oral activity. (White, 1994; van Agtmael et al., 1999). Although many synthetic antimalarial 1,2,4-trioxanes have since been prepared (Cumming et al., 1996;Jefford, 1997), there exists a need in the art to identify new peroxide antimalarial agents, especially those which are easily synthesized, are devoid of neurotoxicity, and which possess improved pharmacokinetic properties, e.g. improved stability, oral absorption, etc.

Accordingly, it is a primary objective of the present invention to provide compositions and methods for prophylaxis and treatment of malaria using spiro and dispiro 1,2,4-trioxolanes.

It is a further objective of the present invention to provide a composition and method for prophylaxis and treatment of malaria using spiro and dispiro 1,2,4-trioxolanes that is nontoxic.

It is a further objective of the present invention to provide a composition and method for prophylaxis and treatment of malaria using spiro and dispiro 1,2,4-trioxolanes that is metabolically stable and orally active.

It is yet a further objective of the present invention to provide a composition and method for prophylaxis and cost-effective treatment of malaria using spiro and dispiro 1,2,4-trioxolanes that do not involve a treatment regimen of more than three days.

It is a further objective of the present invention to provide compositions and methods for prophylaxis and treatment of malaria using spiro and dispiro 1,2,4-trioxolanes that can be used either as stand-alone medicaments or in combination with other agents.

It is still a further objective of the present invention to provide novel intermediates for synthesizing compositions for prophylaxis and treatment of malaria.

The method and means of accomplishing each of the above objectives as well as others will become apparent from the detailed description of the invention which follows hereafter.

SUMMARY OF THE INVENTION

The invention describes a method and composition for treating malaria with spiro and dispiro 1,2,4-trioxolanes, their prodrugs and analogues. The trioxolanes of this invention are sterically hindered on one side of the trioxolane heterocycle in order to provide chemical and metabolic stability to the trioxolane ring for better in vivo activity. In one embodiment, the spiro and dispiro trioxolanes are sterically hindered with an unsubstituted, mono-, di-, or polysubstituted $C_5$-$C_{12}$ Spiro cycloalkyl group, which may be spiroadamantane. In this embodiment, the spiro and dispiro trioxolanes may include a spirocyclohexyl that is functionalized or substituted at the 4-position or a spiropiperidyl ring that is functionalized or substituted at the nitrogen atom. In another embodiment, the trioxolanes of this invention include an alkyl bridge from the 4-position of the spirocyclohexyl ring connecting a substituent that is most preferably a weak base. The invention embraces achiral, achiral diastereomers, racemic mixtures, as well as enantiomeric forms of the compounds.

The trioxolanes of this invention possess excellent potency and efficacy against *Plasmodium* parasites, and a low degree of neurotoxicity. In addition, several of the trioxolanes are suitable for both oral and non-oral administration. Moreover, in comparison to artemisinin semisynthetic derivatives, the compounds of this invention are structurally simple, easy and inexpensive to synthesize, and can be used effectively alone or in conjunction with other antimalarials.

DETAILED DESCRIPTION OF THE PREFERRED EMBODIMENT

The present invention relates to the development of spiro and dispiro 1,2,4-trioxolanes for use in the prophylaxis and treatment of malaria. The present invention is predicated upon the unexpected discovery that trioxolanes that are relatively sterically hindered on at least one side of the trioxolane heterocycle provide metabolic and chemical stability to the trioxolane ring, thereby providing better in vivo activity, especially with respect to oral administration.

As used herein the term "prophylaxis-effective amount" refers to a concentration of compound of this invention that is effective in inhibiting or preventing infection and subsequent disease by malarial parasites. Likewise, the term "treatment-effective amount" refers to a concentration of compound that is effective in treating malaria in terms of preventing an increase in the concentration of malarial parasites, decreasing the concentration of malarial parasites, and/or "curing" a malaria infection, i.e. survival for 30 days post-infection.

Tetrasubstituted trioxolanes are relatively stable peroxidic compounds based on literature precedent (Griesbaum et al., 1997a; 1997b). This may be due, in part, to the lack of α-hydrogen atoms. The present inventors have synthesized new compounds in the trioxolane class having both superior antimalarial potency and oral efficacy. Furthermore, the compounds of this invention have low toxicity, and half-lives conducive to treatment of malaria which are believed will permit short-term treatment regimens comparing favorably to other artemisinin-like drugs. These compounds may also be used in malaria prophylaxis.

In previous application, the present inventors disclosed certain novel tetrasubstituted trioxolanes having the following structural formula:

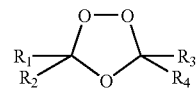

wherein $R_1$, $R_2$, $R_3$, and $R_4$ represent combinations of ring systems, acyclic systems, and functional groups that provide sufficient steric hindrance about the trioxolane ring in order to give the ring chemical and metabolic stability. $R_1$, $R_2$, $R_3$ and $R_4$ may be the same or different, and may be a linear or branched alkyl, aryl, or alkaryl group which is optionally substituted. In the alternative, $R_1$ and $R_2$ taken together and/or $R_3$ and $R_4$ taken together may form an alicyclic group which is optionally interrupted by one or more oxygen, sulfur or nitrogen atoms and which group is optionally substituted. In no event may any of $R_1$, $R_2$, $R_3$ or $R_4$ be hydrogen.

In one embodiment, the compounds include those whereby $R_1$ and $R_2$ taken together and/or $R_3$ and $R_4$ taken together is a mono- or di-substituted $C_5$-$C_{12}$ spirocycloalkyl group which is optionally interrupted by one or more oxygen, sulfur, or nitrogen atoms, and which group is optionally substituted. In another embodiment, $R_1$ and $R_2$ taken together or $R_3$ and $R_4$ is spiroadamantane.

The present invention discloses a new embodiment of trioxolane compounds having the following structure:

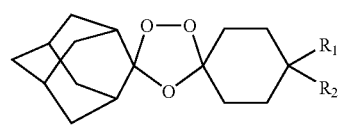

The spirocyclohexyl ring may be optionally interrupted by one or more oxygen, sulfur or nitrogen atoms. In this regard, $R_1$ and $R_2$ may be the same or different, and may be hydrogen, substituted or unsubstituted linear or branched alkyl, aryl, and alkaryl groups and substituted or unsubstituted alicyclic groups that may be interrupted by one or more oxygen, sulfur or nitrogen atoms, substituted or unsubstituted aromatic or heterocyclic groups that may be interrupted by one or more oxygen, sulfur or nitrogen atoms, a hydroxy group, or a halogen. In one embodiment, $R_1$ or $R_2$ is an amide. It has been unexpectedly found that amide-containing substituents at the 4-position provide antimalarial compounds with good oral absorption, good antimalarial activity, and good pharmacokinetics, i.e. rates of absorption, metabolism, and elimination that are suitable and advantageous for the prophylaxis and treatment of malaria.

In another embodiment, the compounds of this invention have the following structural formula:

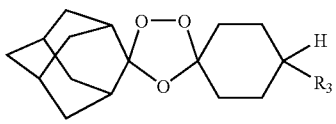

whereby $R_3$ is $(CH_2)_n$—Y. In this formula, Y represents a functional group that, in one embodiment, is non-acidic, and in another embodiment is a weak base. The Y functional group may be an alkyl, ketone, acid, alcohol, amine, amide, sulfonamide, guanidine, ether, ester, oxime, urea, oxime ether, sulfone, lactone, carbamate, semicarbazone, phenyl, or heterocycle. In one embodiment, n=1. The alkyl "bridge" group has been found to improve the metabolically stability (i.e. oral activity and pharmacokinetics) of the antimalarial compounds of this invention.

In another embodiment of the invention, the trioxolanes are weak bases, which provide an ideal combination of high intrinsic potency and good oral activity. Two promising trioxolane structural subtypes are weak base amides of trioxolane amine OZ209 and trioxolane acid OZ78. These compounds have one of the following structural formulas:

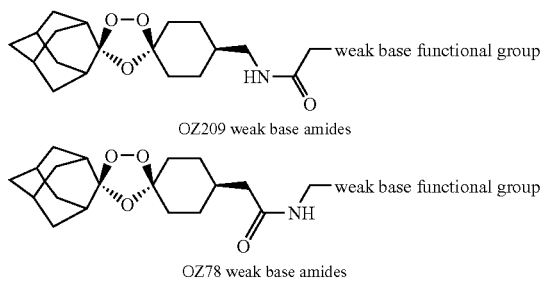

OZ209 weak base amides

OZ78 weak base amides

A more generalized formula for these compounds is as follows:

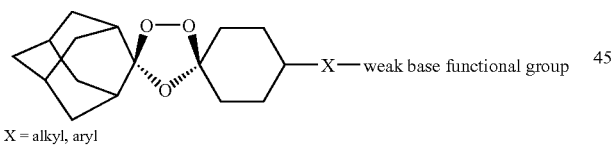

X = alkyl, aryl

Other substituents at the 4-position of the spirocyclohexyl ring are also possible that fall within the scope of this invention. For example, the spirocyclohexyl ring may also be substituted at other positions besides the 4-position. For instance, the inventors have synthesized several compounds substituted at the 2-position of the spirocyclohexyl ring that provide excellent antimalarial potency.

In another embodiment of this invention, the compounds include an alkyl group connecting the substituent at the 4-position to the spirocyclohexyl ring. In one embodiment, the alkyl group is methyl or ethyl. In another embodiment, the alkyl group is methyl. The substituent may also be directly attached to the 4-position of the spirocyclohexyl ring. In another embodiment of this invention, the connecting group for the substituent at the 4-position is an aromatic.

The present inventors have identified two orally active lead dispiro-1,2,4-trioxolanes, OZ03 and OZ05:

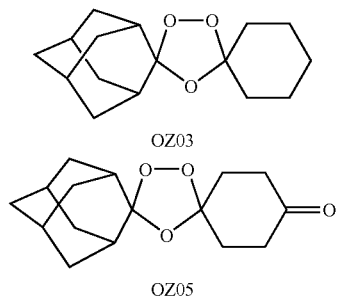

These trioxolanes have $IC_{50s}$ between 1 and 5 ng/ml against *P. falciparum* in vitro, and presumably possess good therapeutic indices as no toxicity is evidence for either compound in a neuroblastoma cell line or at single 640 mg/kg doses in mice in the Rane test. These results contrast with published data (de Almeida Barbosa et al., 1992; 1996) disclosing the weak in vitro antimalarial potency of several tricyclic trioxolanes, the best of which has an $IC_{50}$ of 2000 ng/ml against *P. falciparum* in vitro.

A notable feature of these trioxolanes in comparison to the artemisinin semisynthetic derivatives is their structural simplicity. A potential advantage of trioxolanes over both trioxanes (Jefford, 1997; Cumming et al., 1997) and tetraoxanes (Vennerstrom et al., 2000) is a more convenient access to structurally diverse, non-symmetrical, and in many cases, achiral compounds.

Below are several dispiro 1,2,4-trioxolanes synthesized in accordance with the teachings of this invention. "OZ" is an internal designation for these compounds that will be used throughout the remainder of the application for convenience. The structures of OZ01-OZ369 have been previously disclosed in prior applications U.S. Ser. No. 09/886,666 (U.S. Pat. No. 6,486,199), PCT/US02/19767, U.S. Ser. No. 10/642,721 (U.S. Pat. No. 6,825,230), and U.S. Ser. No. 10/742,010, and are therefore not repeated here.

OZ Series 42 (OZ370-OZ378)

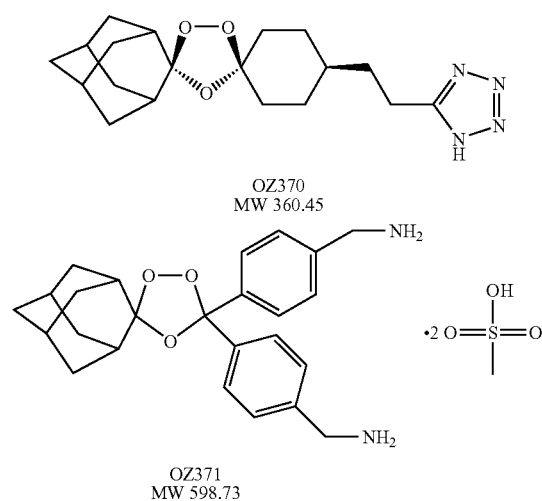

-continued
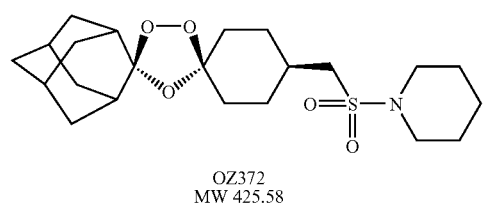
OZ372
MW 425.58
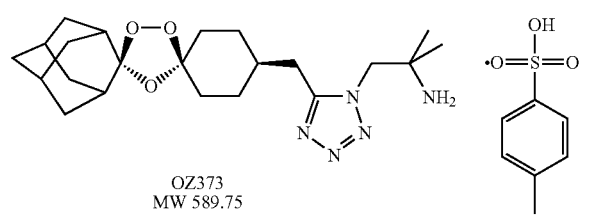
OZ373
MW 589.75
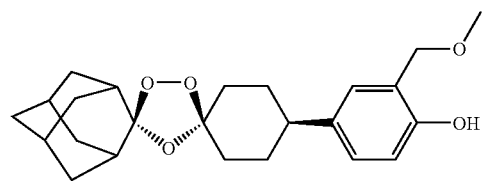
OZ374
MW 400.51
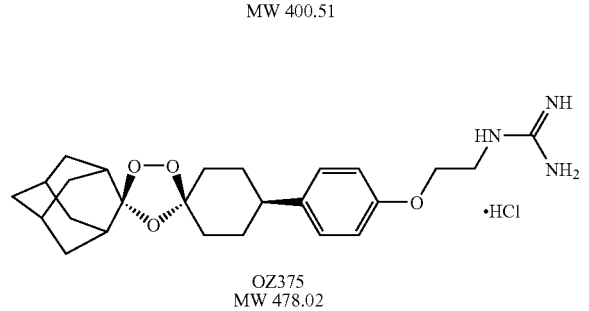
OZ375
MW 478.02
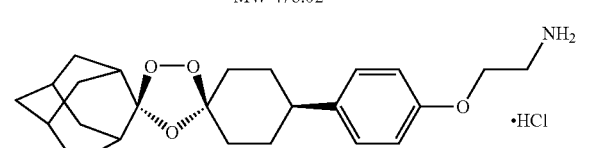
OZ376 (OZ323b)
MW 435.98
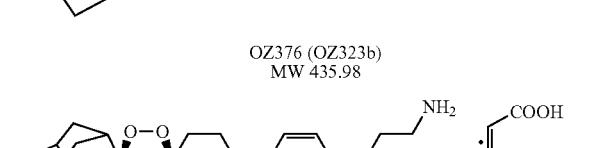
OZ377 (OZ323c)
MW 515.60
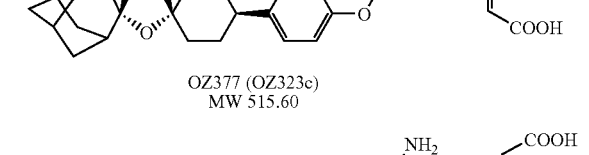
OZ378 (OZ323d)
MW 591.65
OZ Series 43 (OZ379-OZ387)
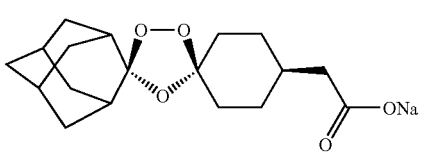
OZ379 (OZ78b)
MW 344.38
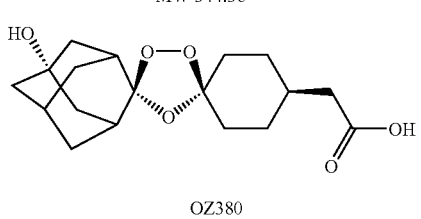
OZ380
MW 338.40
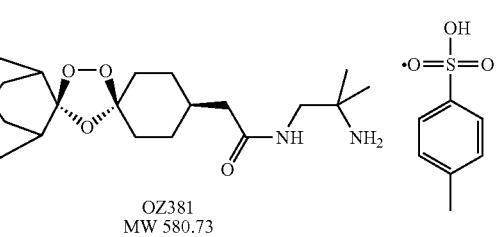
OZ381
MW 580.73
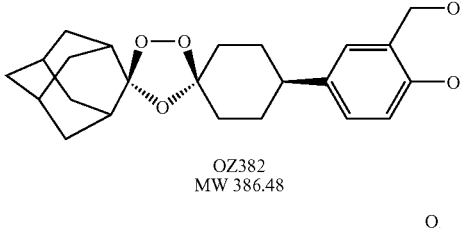
OZ382
MW 386.48
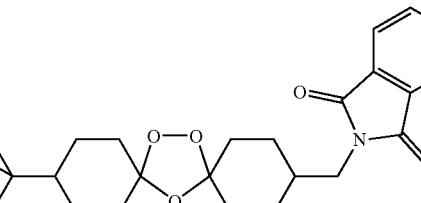
OZ383
MW 427.53
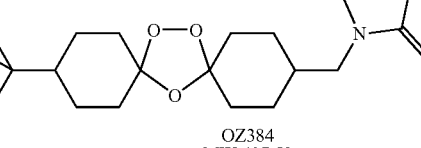
OZ384
MW 427.53
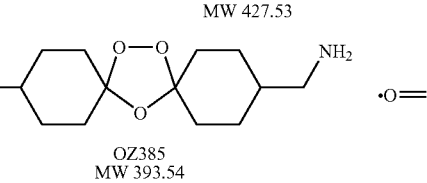
OZ385
MW 393.54

-continued
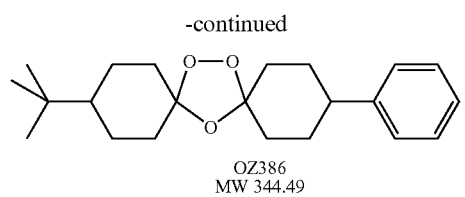
OZ386
MW 344.49
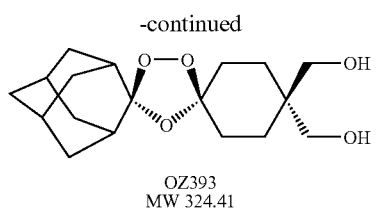
OZ393
MW 324.41
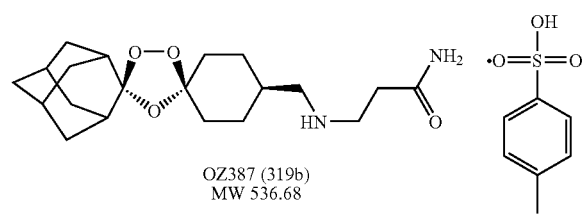
OZ387 (319b)
MW 536.68
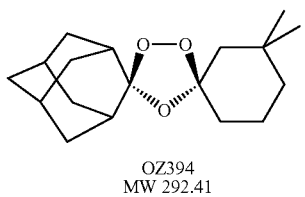
OZ394
MW 292.41
OZ Series 44 (OZ388-OZ396)
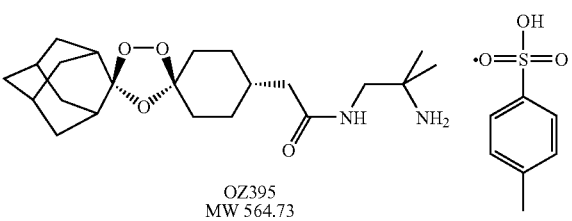
OZ395
MW 564.73
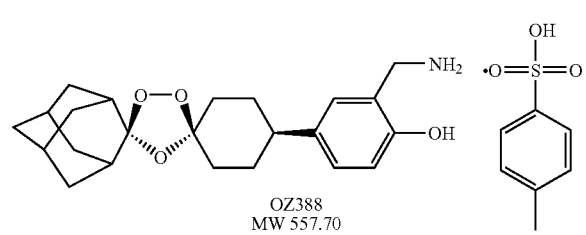
OZ388
MW 557.70
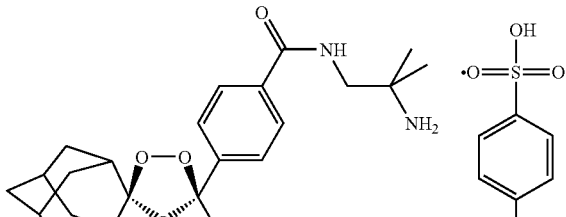
OZ396
MW 634.78
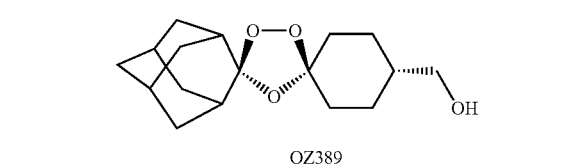
OZ389
MW 294.39
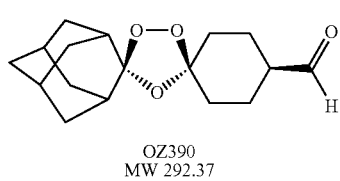
OZ390
MW 292.37
OZ Series 45 (OZ397-OZ405)
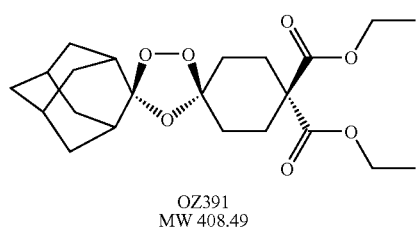
OZ391
MW 408.49
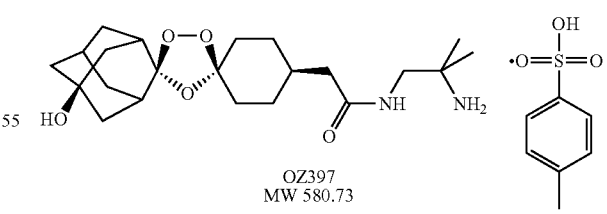
OZ397
MW 580.73
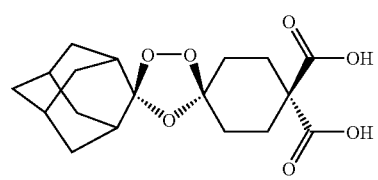
OZ392
MW 352.38
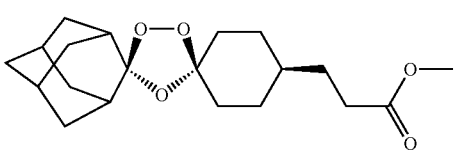
OZ398
MW 350.45

-continued

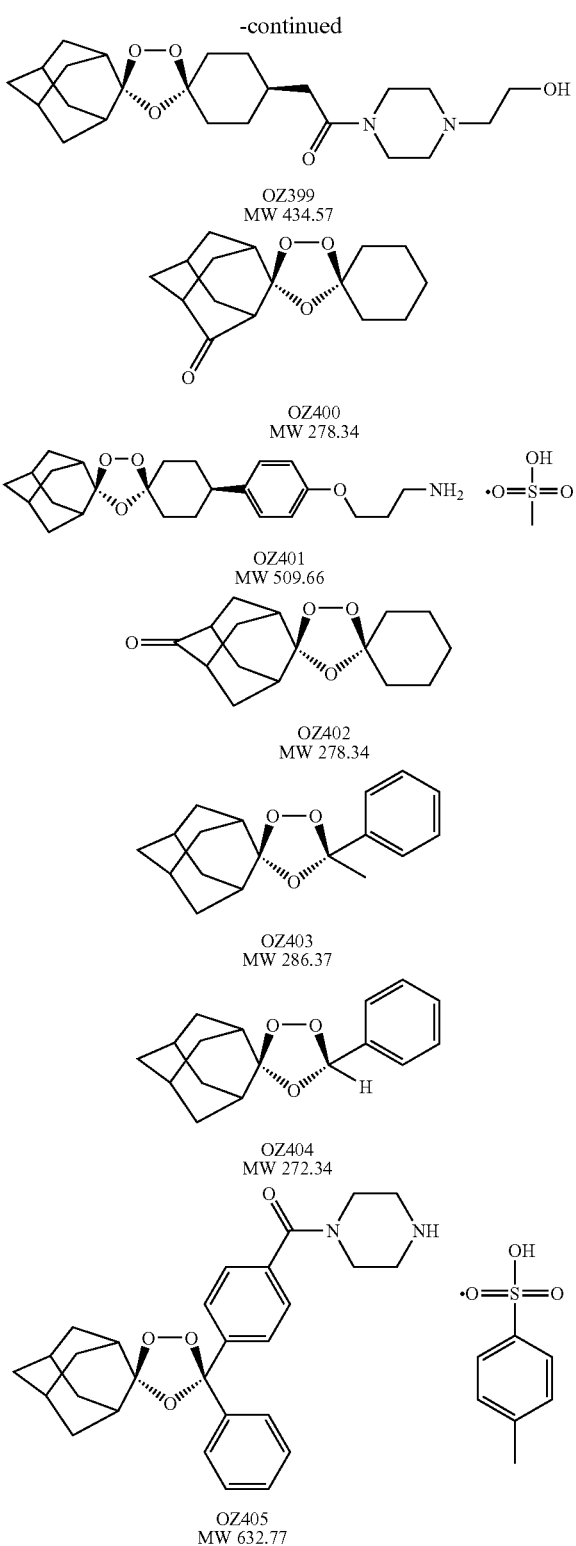

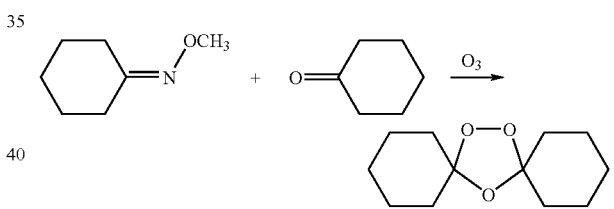

The prototype trioxolanes of this invention are OZ03 and OZ05. Preferred compounds identified thus far include OZ03, OZ05, OZ11, OZ25, OZ27, OZ61, OZ71, OZ78, OZ127, OZ145, OZ156, OZ163, OZ175, OZ177, OZ179, OZ181, OZ189, OZ205, OZ207, OZ209, OZ210, OZ219, OZ227, OZ229, OZ235, OZ255, OZ256, OZ257, OZ263, OZ264, OZ265, OZ266, OZ267, OZ268, OZ269, OZ270, OZ271, OZ277, OZ281, OZ279, OZ288, OZ289, OZ290, OZ296, OZ297, OZ298, OZ301, OZ305, OZ309, OZ315, OZ317, OZ319, OZ320, OZ323, OZ329, OZ333, OZ335, OZ336, OZ337, OZ338, OZ339, OZ343, OZ349, OZ351, OZ353, OZ354, OZ357, OZ358, OZ359, OZ365, OZ368, OZ376, OZ377, OZ378, OZ387, OZ388, OZ396, OZ399, OZ401, and OZ405. The most preferred compounds are OZ78, OZ163, OZ181, OZ207, OZ209, OZ255, OZ256, OZ257, OZ263, OZ264, OZ267, OZ271, OZ277, OZ279, OZ301, OZ305, OZ315, OZ317, OZ319, OZ323, OZ329, OZ338, OZ339, OZ349, OZ351, OZ354, OZ357, OZ359, OZ368, OZ376, OZ377, OZ378, OZ387, and OZ401, with OZ277 and OZ279 being the best of those compounds identified thus far. It should be noted that OZ376-378 are different salts from OZ323 (mesylate). Further, OZ387 is the tosylate salt of OZ319 (mesylate).

In general, the highest in vitro potency against malarial parasites is obtained for trioxolanes functionalized or substituted at the 4-position of the spirocyclohexyl ring. As a general rule, non-symmetrical, achiral trioxolanes are also preferred.

Notable features of these spiro and dispiro 1,2,4-trioxolanes in comparison to the artemisinin semisynthetic derivatives are their structural simplicity and ease of synthesis. For example, dispiro trioxolanes may be easily synthesized by the coozonolysis of the O-methyl oximes of cycloalkanones in the presence of the requisite cycloalkanone derivatives according to the method of Griesbaum et al. (1997a; 1997b) as illustrated below for the symmetrical dispiro cyclohexyl trioxolane:

If yields are low in this coozonolysis reaction, yields can improve dramatically when the O-methyloxime and ketone are "reversed." This novel procedure provides a uniquely convenient method to synthesize spiro and dispiro trioxolanes. Advantages of the oxime ether route over the alkene approach include convenient synthesis of starting materials (oxime ethers vs. tetrasubstituted alkenes), higher yield and selectivity of formation of desired trioxolanes by the judicious selection of paired reaction substrates. The trioxolanes may be purified by crystallization or by flash column chromatography. Their structures and purity may be confirmed by analytical HPLC, $^1$H and $^{13}$C NMR, IR, melting point and elemental analysis.

Formation of a trioxolane from an oxime ether and a ketone is presumed to be a three-step process. The sequence begins by the electrophilic addition of ozone to the oxime double bond to form a primary ozonide. Second, the very unstable primary adduct fragments to a reactive carbonyl oxide driven in part by the concomitant expulsion of the relatively stable methyl nitrite. Third, the carbonyl oxide undergoes a [3+2] cycloaddition with a ketone to give the secondary ozonide or 1,2,4-trioxolane. It remains to be

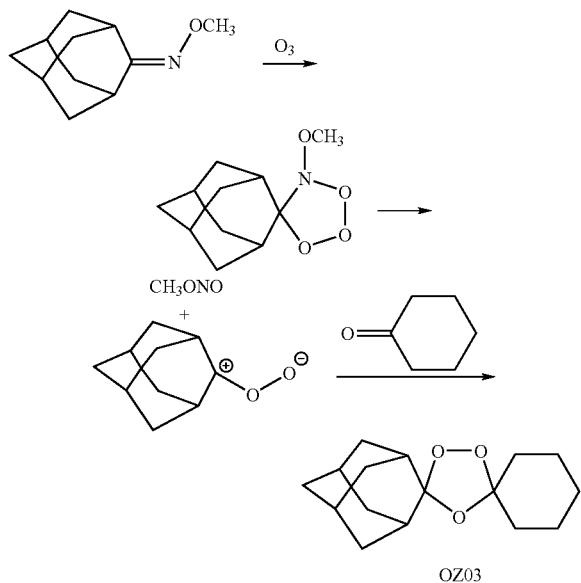

determined whether this is a stepwise or a concerted recombination process.

As illustrated above by the synthesis of OZ03, most of the new dispiro trioxolanes contain a spiroadamantane and can be synthesized by the coozonolysis of adamantanone O-methyl oxime in the presence of the requisite cycloalkanone derivative. The preferred reaction solvents for the coozonolysis reactions are hydrocarbon solvents such as pentane or cyclohexane; more polar solvents tend to decrease the yield of the reaction. When ketones are not readily soluble in pentane or cyclohexane, a mixed solvent (pentane/methylene chloride) or methylene chloride alone may be used. Several factors govern the ratio of oxime ether to ketone. In some reactions, in order to avoid diperoxide (1,2,4,5-tetraoxane) formation, to preclude diozonide formation from diketones, and to promote the reaction with readily pentane soluble ketones, excess ketone (2:1) is used. Most commonly in the discovery synthesis stage, and especially in cases where ketones are not readily soluble in pentane, expensive, or difficult to remove in the reaction workup, a 1:1 ratio of ketone to oxime ether may be used. In large scale trioxolane syntheses, a 1.5-fold excess of oxime ether can be used to achieve higher conversions of ketones into the desired product trioxolanes without causing purification problems.

The Spiro and dispiro trioxolane compositions of the present invention may be generally used for the prophylaxis and treatment of malaria. The trioxolane compositions of the present invention are administered along with a pharmaceutically acceptable carrier. Any pharmaceutically acceptable carrier may be generally used for this purpose, provided that the carrier does not significantly interfere with the stability or bioavailability of the trioxolane compounds of this invention.

The trioxolanes of this invention can be administered in any effectively pharmaceutically acceptable form to warm blooded animals, including human and other animal subjects, e.g. in topical, lavage, oral, suppository, parenteral, or infusible dosage forms, as a topical, buccal, sublingual, or nasal spray or in any other manner effective to deliver the agents. The route of administration will preferably be designed to optimize delivery and/or localization of the agents to target cells.

In addition to the active compounds i.e. the trioxolanes, the pharmaceutical compositions of this invention may contain suitable excipients and auxiliaries which facilitate processing of the active compounds into preparations which can be used pharmaceutically. Oral dosage forms encompass tablets, capsules, and granules. Preparations which can be administered rectally include suppositories. Other dosage forms include suitable solutions for administration parenterally or orally, and compositions which can be administered buccally or sublingually.

The pharmaceutical preparations of the present invention are manufactured in a manner which is itself well known in the art. For example the pharmaceutical preparations may be made by means of conventional mixing, granulating, dragee-making, dissolving, lyophilizing processes. The processes to be used will depend ultimately on the physical properties of the active ingredient used.

Suitable excipients are, in particular, fillers such as sugars for example, lactose or sucrose mannitol or sorbitol, cellulose preparations and/or calcium phosphates, for example, tricalcium phosphate or calcium hydrogen phosphate, as well as binders such as starch, paste, using, for example, maize starch, wheat starch, rice starch, potato starch, gelatin, gum tragacanth, methyl cellulose, hydroxypropylmethylcellulose, sodium carboxymethylcellulose, and/or polyvinyl pyrrolidone. If desired, disintegrating agents may be added, such as the above-mentioned starches as well as carboxymethyl starch, cross-linked polyvinyl pyrrolidone, agar, or alginic acid or a salt thereof, such as sodium alginate. Auxiliaries are flow-regulating agents and lubricants, for example, such as silica, talc, stearic acid or salts thereof, such as magnesium stearate or calcium stearate and/or polyethylene glycol. Oral dosage forms may be provided with suitable coatings which, if desired, may be resistant to gastric juices.

For this purpose concentrated sugar solutions may be used, which may optionally contain gum arabic, talc, polyvinylpyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, dyestuffs and pigments may be added to the tablet coatings, for example, for identification or in order to characterize different combination of compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, liquid paraffin, or liquid polyethylene glycols. In addition stabilizers may be added. Possible pharmaceutical preparations which can be used rectally include, for example, suppositories, which consist of a combination of the active compounds with the suppository base. Suitable suppository bases are, for example, natural or synthetic triglycerides, paraffin hydrocarbons, polyethylene glycols, or higher alkanols. In addition, it is also possible to use gelatin rectal capsules which consist of a combination of the active compounds with a base. Possible base material include for example liquid triglycerides, polyethylene glycols, or paraffin hydrocarbons.

Suitable formulations for parenteral administration include aqueous solutions of active compounds in water-soluble or water-dispersible form. In addition, suspensions of the active compounds as appropriate oily injection suspensions may be administered. Suitable lipophilic solvents or vehicles include fatty oils for example, sesame oil, or synthetic fatty acid esters, for example, ethyl oleate or triglycerides. Aqueous injection suspensions may contain substances which increase the viscosity of the suspension, including for example, sodium carboxymethyl cellulose, sorbitol and/or dextran. Such compositions may also comprise adjuvants such as preserving, wetting, emulsifying, and dispensing agents. They may also be sterilized, for example, by filtration through a bacteria-retaining filter, or by incorporating sterilizing agents into the compositions. They can also be manufactured in the form of sterile solid compositions which can be dissolved or suspended in sterile water, saline, or other injectable medium prior to administration.

In addition to administration with conventional carriers, active ingredients may be administered by a variety of specialized delivery drug techniques which are known to those of skill in the art, such as portable infusion pumps.

The trioxolane compositions of the present invention are administered along with a pharmaceutically acceptable carrier in an amount sufficient to prevent malarial infection and/or treat an active infection. The trioxolane compounds of this invention have extremely low toxicity and a low degree of side effects even at high doses. The dosing range of the trioxolane compositions will vary depending on a number of factors, such as whether it is used for prophylaxis or treatment of an active infection, route of administration, dosing schedule, etc. In general, the therapeutic dose of trioxolane may range between about 0.1-1000 mg/kg/day, with between about 1-100 mg/kg/day being preferred. The foregoing doses may be administered as a single dose or may be divided into multiple doses for administration. The trioxolane compositions may be administered once to several times daily. For malaria prevention, a typical dosing schedule could be, for example, 2.0-1000 mg/kg weekly beginning 1-2 weeks prior to malaria exposure taken up until 1-2 weeks post-exposure.

The spiro and dispiro trioxolanes of this invention may be administered as any pharmaceutically effective salt form. Such salts are well known in the art and include, but are not limited to acetate, adipate, alginate, citrate, aspartate, benzoate, benzene sulfonate, bisulfate, butyrate, camphorate, camphor sulfonate, digluconate, glycerophosphate, hemisulfate, heptanoate, hexanoate, fumarate, hydrochloride, hydrobromide, hydroiodide, 2-hydroxyethansulfonate (isothionate), lactate, maleate, methane sulfonate, nicotinate, 2-naphthalene sulfonate, oxalate, palmitoate, pectinate, persulfate, 3-phenylpropionate, picrate, pivalate, propionate, succinate, tartrate, thiocyanate, phosphate, glutamate, bicarbonate, p-toluene sulfonate and undecanoate salts. Preferred salts are those that increase the bioavailability of the trioxolane compounds. This will depend upon a number of factors, including the chemical structure of the trioxolane, the carrier to which it is incorporated, the route of administration, etc.

The spiro and dispiro trioxolanes of this invention have been found to be effective in the treatment of schistosomiasis. Schistosomiasis ranks second behind malaria in terms of socioeconomic and public health importance in tropical and subtropical areas. The disease is endemic in 74 developing countries, infecting more than 200 million people in rural agricultural and peri-urban areas. An estimated 500-600 million people worldwide are at risk from the disease.

The major forms of human schistosomiasis are caused by five species of water-borne flatworm, or blood flukes, called schistosomes. One of these species is *Schistosoma mansoni*, which has been reported in 53 countries in Africa, the Eastern Mediterranean, the Caribbean, and South America. The parasites enter the body through contact with infested surface water, primarily among people engaged in agriculture and fishing. The parasites normally infect the host during the cercaria, or larval stage. Once inside the host, the cercaria develop into adults or schistosomes.

Current treatments for schistosomiasis have focused primarily on prophylaxis, i.e. prevention of host infection by cercaria. Currently, praziquantel is the most widely used drug for treatment of schistosomiasis. While artemether has demonstrated activity in the prophylaxis of schistosomiasis, it has not shown any activity against adult *S. mansoni*.

It has now been unexpectedly discovered that the spiro and dispiro trioxolanes of this invention are active against both cercaria and adult *S. mansoni, S. japonicum* when administered in the dosages and manner outlined above with respect to treatment of malarial parasites. It is also believed the trioxolanes of this invention will be active against *S. haematobium*. Preferred compounds identified for use in the treatment of schistosomiasis include OZ05, OZ11, OZ23, OZ25, OZ28, OZ32, OZ71, OZ78, OZ89, OZ90, OZ119, OZ145, OZ179, OZ205, OZ207, OZ209, OZ376, OZ377, OZ378, OZ382, OZ383, OZ388, and OZ401. Most preferred compounds are OZ78, OZ207, and OZ209. Preferred dosing levels of the spiro and dispiro trioxolanes are about 100-200 mg/kg/day orally. The prototype trioxolanes of this invention are OZ03 and OZ05.

The spiro and dispiro trioxolanes of this invention may also have effectiveness in the treatment of cancer. Compounds having an endoperoxide moiety that is reactive with heme and iron have shown an ability to kill cancer cells. (See e.g. U.S. Pat. No. 5,578,637, the disclosure of which is hereby incorporated by reference). As noted with respect to artemisinin, trioxolanes' mechanism of action against malarial parasites is based on the ability of trioxolane compounds to react with the iron in free heme molecules in malaria parasites, with the generation of free radicals leading to cellular destruction. Similarly, trioxolanes are selective against cancer cells due to the higher concentration of transferrin receptors on cancer cell membranes that pick up iron at a higher rate than normal cells. In the presence of the trioxolanes of this invention, the cancer cells will accumulate high concentrations of free radicals, leading to cell death. For cancer treatment, the trioxolanes of this invention may be administered in the doses and manner outlined above.

Other drugs besides trioxolanes which are compatible with the carrier ingredients may also be incorporated into the carrier. Such drugs may be readily ascertained by those of ordinary skill in the art and may include, for instance, antibiotics, other antimalarials, antiinflammatory agents, etc.

It is understood that the present invention contemplates the use of not only the above-stated trioxolane compounds themselves, but their prodrugs which metabolize to the compound and the analogues and biologically active salt forms thereof, as well as optical isomers which provide the same pharmaceutical results.

The following examples are offered to illustrate but not limit the invention. Thus, they are presented with the understanding that various formulation modifications as well as method of delivery modifications may be made and still be within the spirit of the invention.

EXAMPLE 1

Antimalarial Activity of OZ370-OZ405

Antimalarial Assays

Each trioxolane was screened against the chloroquine-resistant K1 and chloroquine-sensitive NF54 strains of *Plasmodium falciparum* in vitro. In the single dose in vivo screen, NMRI mice infected with the ANKA strain of *P. berghei* (groups of five mice) were treated one day post-infection with trioxolanes dissolved or suspended in standard suspending vehicle (SSV). The SSV consists of 0.5% w/v CMC, 0.5% v/v benzyl alcohol, 0.4% v/v Tween 80, and 0.9% w/v sodium chloride in water. Trioxolanes are administered as single 10 and 3 mg/kg po doses. Antimalarial activity was measured by percent reduction in parasitemia on day three post-infection and survival times compared to an untreated control group. Survival to day 30 post-infection is considered to be a cure. For comparative analysis, data is also presented for the control antimalarial drugs artemether (AM), artesunate (AS), chloroquine (CQ), and mefloquine (MFQ).

Below is the activity data for OZ370-OZ405.

TABLE 1

| Compd | $IC_{50}$ (ng/ml) K1/NF54 | Activity (%) 10/3 mg/kg | Survival (days) 10/3 mg/kg |
|---|---|---|---|
| NONE | — | 0 | 6.0 to 7.0 |
| OZ370 | 19/8.2 | 94/40 | 9.0/6.8 |
| OZ371 | 11/5.6 | 98/14 | 10.8/6.2 |
| OZ372 | 2.4/1.8 | 19/36 | 6.6/7.0 |
| OZ373 | 2.3/1.5 | 98/74 | 10.0/7.8 |
| OZ374 | 4.9/4.3 | 85/29 | 9.8/6.8 |
| OZ375 | 15/9.1 | 18/0 | 6.8/6.2 |
| OZ376 | 1.3/1.1 | 99.95/98 | 21.0/10.8 |
| OZ377 | 1.8/1.4 | 99.98/99.78 | 20.8/11.2 |
| OZ378 | 2.1/1.3 | 100/96 | 21.6/10.4 |
| OZ379 | 45/43 | 60/17 | 8.6/7.0 |
| OZ380 | >100/>100 | 0/0 | 7.8/8.6 |
| OZ381 | >100/>100 | 0/0 | 7.4/7.0 |
| OZ382 | 4.1/3.5 | 97/36 | 10.4/7.2 |
| OZ383 | 4.3/3.7 | 0/0 | 7.6/7.0 |
| OZ384 | >100/>100 | 0/0 | 7.0/7.0 |
| OZ385 | >100/>100 | 0/0 | 7.4/7.4 |
| OZ386 | 77/62 | 0/0 | 7.2/7.0 |
| OZ387 | 1.0/0.86 | 99.87/94 | 7/4/9.4 |
| OZ388 | 1.0/1.2 | 99.91/99.02 | 9.8/11.0 |
| OZ389 | 0.71/0.83 | 99/52 | 11.4/8.4 |
| OZ390 | 6.0/7.4 | 97/60 | 12.0/8.4 |
| OZ391 | 2.6/3.0 | 9/0 | 7.6/7.4 |
| OZ392 | >100/>100 | 0/0 | 7.4/7.6 |
| OZ393 | 0.85/1.2 | 84/10 | 10.6/7.8 |
| OZ394 | 2.5/2.5 | 88/9 | 10.0/8.0 |
| OZ395 | 1.7/1.5 | 96/56 | 11.4/8.8 |
| OZ396 | 3.2/3.1 | 99.89/88 | 11.6/10.0 |
| OZ397 | 110/81 | ND/14 | ND/6.2 |
| OZ398 | 6.3/6.0 | ND/12 | ND/6.2 |
| OZ399 | 1.0/0.90 | ND/85 | ND/6.4 |
| OZ400 | 35/42 | 26/28 | 6.2/6.4 |
| OZ401 | 1.9/1.7 | ND/99.65 | ND/7.0 |
| OZ402 | 5.5/5.1 | 17/24 | 6.2/6.0 |
| OZ403 | 2.9/3.4 | 99[1] | 7.2[1] |
| OZ404 | 400/>1000 | 25[1] | 6.2[1] |
| OZ405 | 2.1/2.4 | ND/95 | ND/6.0 |
| AM | 0.45/0.36 | 99.75/79 | 9.4/8.7 |
| AS | 1.4/1.5 | 87/66 | 7.0/8.0 |
| CQ | 76/4.4 | 99.92/82 | 9.0/8.0 |
| MFQ | 2.2/5.0 | 99.11/9 | 17/6.3 |

[1]data from a single 100 mg/kg po dose (3% ethanol and 7% Tween 80 vehicle)

The new activity data demonstrates that trioxolane carboxylic acids are usually less active than their hydrocarbon, ester, and amide counterparts. The best combination of high intrinsic potency and good oral activity is found when a weak base functional group is present.

EXAMPLE 2

Effect of Trioxolanes On *Schistosoma* Species

Effect of Trioxolane OZ207 On *Schistosoma japonicum*

TABLE 2

Comparative effect of OZ207 and artemether in mice infected with *Schistosoma japonicum*

| Drug | Age of worm | Dose (mg/kg × 1) | Mice without ♀ worm | MTWB/ x ± SD | WRR/% | MFWB/ x ± SD | FWRR/% |
|---|---|---|---|---|---|---|---|
| Control | — | — | 0/8 | 26.6 ± 4.2 | — | 11.6 ± 2.4 | — |
| OZ207 | 35 days | 200 | 4/7 | 9.1 ± 3.9 | 66 | 0.6 ± 0.7 | 95 |
| OZ207 | 35 days | 400 | 4/6 | 4.3 ± 1.2 | 84 | 0.7 ± 1.2 | 94 |
| Artemether | 35 days | 400 | 0/7 | 10.1 ± 4.4 | 62 | 3.4 ± 1.6 | 71 |
| OZ207 | 7 days | 200 | 0/8 | 5.4 ± 2.4 | 81 | 2.1 ± 1.0 | 82 |

MTWB, mean total worm burden;
WRR, worm reduction rate
MFWB, mean female worm burden;
FWRR, female worm reduction rate.

Table 3 illustrates that the mean total worm burden and mean female worm burden in OZ207 400 mg/kg group was significantly lower than those in artemether 400 mg/kg group (P<0.01). The mean female worm burden in OZ207 200 mg/kg group was also significantly lower than that in artemether group (P<0.01).

Effect of Trioxolanes On 21-Day-Old Schistosomules

Mice were infected with 100 *Schistosoma mansoni* cercariae on day 21 post-treatment. Each group was treated per os with trioxolanes at a single dose of 200 mg/kg. Untreated mice served as the control. All groups were killed 4 weeks after treatment and the liver and intestine were removed and separated. The liver and intestine were compressed and live male and female worms could be seen and counted. The effect of the compounds was evaluated by mean total and female worm burden. The results are shown in Table 4.

Effect of Trioxolanes On Adult Schistosomes (49-day-old)

Mice were infected with 100 *Schistosoma mansoni* cercariae on day 49 post-treatment. Each group was treated per os with OZ compounds at single doses of 200, 400, and 600 mg/kg. Untreated mice served as the control. All groups were killed 4 weeks after treatment and the liver and intestine were removed and separated. The liver and intestine were compressed and alive male and female worms could be seen and counted. The effect of the compounds was evaluated by mean total and female worm burden, and the results are set forth in Table 4.

the standard suspending vehicle (SSV) and administered as single 10, 6, 3, 1, 0.3, and 0.1 mg/kg doses po and sc. The SSV consists of 0.5% w/v CMC, 0.5% v/v benzyl alcohol, 0.4% v/v Tween 80, and 0.9% w/v sodium chloride in water. Antimalarial activity was measured by percent reduction in parasitemia on day three post-infection. The $ED_{50}/ED_{90}$ values were calculated by nonlinear fitting.

TABLE 4

| Compd | $ED_{50}$ (mg/kg) | $ED_{90}$ (mg/kg) | $ED_{99}$ (mg/kg) |
|---|---|---|---|
| OZ277 | 0.78 | 2.0 | 4.4 |
| OZ279 | 0.63 | 1.8 | 3.9 |
| Artesunate | 4.7 | 19 | 60 |
| Artelinate | 4.8 | 10 | 18 |
| Artemether | 2.2 | 4.2 | 7.1 |
| Chloroquine | 1.8 | 3.5 | 5.9 |
| Mefloquine | 4.0 | 5.4 | 6.8 |

Table 4 shows ED50/ED90/ED99 data obtained by po administration of trioxolanes in the SSV formulation. The relatively lipophilic artemether is substantially more active than the more polar artesunate and artelinate. In contrast, the most active trioxolanes (OZ181, OZ207, OZ209)—different salt forms of the same amino trioxolane, and amino and amide trioxolanes OZ277 and OZ279, are relatively polar compounds.

TABLE 3

IN VIVO ACTIVITY AGAINST *SCHISTOSOMA MANSONI* (MICE female INFECTED)

| OZ COMPOUNDS TESTED | % reduction of schistosomule growth at day 21 after per os application of 200 mg/kg | | % reduction of adult worms growth at day 49 after per os application of . . . mg/kg | | | |
|---|---|---|---|---|---|---|
| | TWR (%) | FWR (%) | 200 | 400 TWR (%)/ DEAD WORM (%) | 600 | |
| OZ 271 | 88 | 86 | 0/6 | | | |
| OZ 277 | 91 | 92 | 0/0 | 17/14 | | 1 × 600 sc. 39/17 |
| OZ 279 | 86 | 88 | 0/12 | 33/20 | | 1 × 600 sc. 21/27 |
| OZ 281 | 91 | 90 | 12/15 | | | |
| OZ 285 liquid | 86 | 85 | 17/22 | | | |
| OZ 288 | 95 | 96 | 52/45 | | | |
| OZ 296 | 85 | 85 | 1/13 | | | |
| OZ 309 | 97 | 100 | 19/17 | | | |
| OZ 312 | 94 | 93 | 16/9 | | | |
| OZ 323 | 95 | 97 | 20/3 | | | |
| OZ 329 | 90 | 90 | 15/6 | | | |
| OZ 349 | ND | ND | 36/16 | | | |
| OZ 352 | 89 | 91 | 16/26 | | | |
| OZ 360 | 17 | 13 | 0/0 | | | |
| ARTEMETHER | (n4) 85 | (n4) 85 | (n2) 53/29 | | | |
| PRAZIQUANTEL | 0 | 0 | (n2) 96/96 | 100/100 | | |

EXAMPLE 3

Activity of Trioxolanes Against *P. berghei*

In the single dose $ED_{50}/ED_{90}/ED_{99}$ determinations, Moro SPF or NMRI mice (group of three) infected with the ANKA strain of *Plasmodium berghei* were treated on day one post-infection. Trioxolanes were dissolved or suspended in

EXAMPLE 4

Dosing of OZ279, OZ277, OZ256, and OZ209

Based on results of dosing OZ279, OZ277, OZ256, and OZ209 in rats and dogs, the inventors determined projected optimal dosing of the same compounds in humans. Artesunate is listed as a reference compound.

TABLE 5

| Parameter | Ideal | Accept | Artes | OZ 279 | OZ 277 | OZ 256 | OZ 209 |
|---|---|---|---|---|---|---|---|
| Rat Data | | | | | | | |
| IV t½ (10 mg/kg) | 180 min | 60 min | 40 (DHA) | 100.5 | 77.2 | 94.0 | 150.0 |
| Oral Bioavailability 10 mg/kg | >30% | >20% | not done | 37.2 | 36.9 | 18.6 | 12.4 |
| 25 mg/kg | >30% | >20% | 21 (DHA) | 71.1 | 44.1 | 51.9 | 22.4 |
| Oral t½ (25 mg/kg) | 180 min | 60 min | not done | 166.8 | 90.5 | 73.3 | 101.5 |
| Dog Data | | | | | | | |
| IV t½ (10 mg/kg) | 180 min | 60 min | not done | 177.5 | 95.0 | 85.4 | 182.8 |
| Oral Bioavailability 10 mg/kg | >30% | >20% | not done | 32.8 (V) | 87.9 | 42.0 (V) | 24.5 (V) |
| 25 mg/kg | >30% | >20% | not done | 55.7 (V) | 96.1 | 38.3 (V) | 15.9 (V) |
| Oral t½ (10 mg/kg) | 180 min | 60 min | not done | 195.3 | 148.1 | 82.8 | 127.3 |
| Human Data | | | | | | | |
| Projected daily dose mg/day (% BA) | 150 mg | 300 mg | 150-300 (actual) | 105-154 (30%) | 28-56 (30%) | 91-133 (20%) | 35-70 (20%) |

EXAMPLE 5

Effectiveness of Selected OZ Compounds In The Treatment and Prophylaxis of Malarial Infections Moro NMRI male mice (Fü Albino specific pathogen free) weighing 18±2 g were infected intravenously (i.v.) with $2 \times 10^7$ P. berghei ANKA strain-infected erythrocytes from donor mice on day 0 of the experiment. From donor mice with circa 30% parasitemia, heparinized blood was taken and diluted in physiological saline to $10^8$ parasitized erythrocytes per ml. An aliquot (0.2 ml) of this suspension was injected i.v. into experimental and control groups of mice. In untreated control mice, parasitemia rose regularly to 40 to 50% by day 3 post-infection and 70 to 80% by day 4 post-infection. The mice died between days 5 and 7 post-infection. Throughout the experiments, mice were kept in groups of three or five animals in Makrolon type II cages in an air-conditioned animal room at 22 to 23° C. A diet with p-aminobenzoic acid (PABA) of 45 mg (NAFAG FUTTER© food N° 9009 PAB-45) per kg of body weight, and tap water is available ad libitum.

OZ compounds were prepared at an appropriate concentration, either as a solution or a suspension containing SSV (0.5% w/v CMC, 0.5% v/v benzyl alcohol, 0.4% v/v Tween 80, and 0.9% w/v sodium chloride in water). They were administered per os (p.o.) in a total volume of 0.01 ml per gram of mouse. The activity of the compound was determined by a variety of methods outlined in subsequent sections. Survival time was also recorded, and survival to day 30 post-infection was considered to be a cure. The first experiment conducted consisted of administration of a divided 3×10 mg/kg p.o. dose administered on days 1, 2, and 3 post-infection vs. a single 1×30 mg/kg po dose administered on day 1 post-infection. On day 4 post-infection, blood smears of all animals were prepared and stained with Giemsa. Parasitemia was determined microscopically, and the difference between the mean value of the control group (taken as 100%) and those of the experimental groups was calculated and expressed as percent reduction. Compounds were administered orally in the SSV vehicle. The results are shown in Table 6 below:

TABLE 6

| | 1 × 30 mg/kg | | | 3 × 10 mg/kg | | |
|---|---|---|---|---|---|---|
| OZ | Activity % p.o. | Survival (days) SSV | Cures | Activity (%) p.o. | Survival (days) SSV | Cures |
| 209 | 100 | >30 | 0/5 | 100 | >30 | 3\3 |
| 271 | 99.97 | 14 | 0/5 | 100 | 27.8 | 4\5 |
| 277 | 99.92 | 10.4 | 0/5 | 100 | 27.6 | 4\5 |
| 279 | 99.95 | 14.8 | 0/5 | 100 | 25.4 | 3\5 |
| 301 | NA | NA | NA | 100 | >30 | 5\5 |
| 315 | NA | NA | NA | 100 | >30 | 5\5 |
| CQ | 99.94 | 9.5 | 0/5 | 99.99 | 14.3 | 0/5 |
| M FQ | 99.94 | 20.3 | 0/5 | 99.92 | 23.3 | 0/5 |
| AS | 83.83 | 9 | 0/5 | 98.62 | 11 | 0/5 |

As shown by Table 6, a 3×10 mg/kg dose of these trioxolanes cured between 3/5 and 5/5 of the infected mice. At this same dose, none of the standard antimalarial drugs cured any of the infected mice. At the 1×30 mg/kg dose, all tested trioxolanes showed activities >99.9% on day 3 post-treatment.

The second experiment consists of administration of divided 3×3 mg/kg and 3×1 mg/kg po doses administered on days 1, 2, and 3 post-infection. On day 4 post-infection, blood smears of all animals were prepared and stained with Giemsa. Parasitemia was determined microscopically, and the difference between the mean value of the control group (taken as 100%) and those of the experimental groups was calculated and expressed as percent reduction. Compounds were administered orally in the SSV vehicle. The results are shown in Table 7.

TABLE 7

| | 3 × 3 mg/kg | | | 3 × 1 mg/kg | | |
|---|---|---|---|---|---|---|
| OZ | Activity (%) p.o. | Survival (days) SSV | Cures | Activity (%) p.o. | Survival (days) SSV | |
| 209 | 100 | 16.4 | 0\5 | 99.51 | 9.4 | |
| 271 | 99.99 | 16.2 | 0\5 | 87 | 8.8 | |

TABLE 7-continued

| | 3 × 3 mg/kg | | | 3 × 1 mg/kg | |
|---|---|---|---|---|---|
| OZ | Activity (%) p.o. | Survival (days) SSV | Cures | Activity (%) p.o. | Survival (days) SSV |
| 277 | 100 | 14 | 0\5 | 83 | 9.4 |
| 279 | 100 | 14.8 | 0\5 | 83 | 8.8 |
| 281 | 100 | 12.4 | 0\5 | 92 | 13 |
| 288 | 99 | 10.2 | 0\5 | 49 | 8.4 |
| 289 | 100 | 17.2 | 0\5 | 41 | 7.4 |
| 290 | 93 | 10.6 | 0\5 | 14 | 6.8 |
| 296 | 94 | 9.4 | 0\5 | 49 | 7.8 |
| 297 | 89 | 9.4 | 0\5 | 22 | 6.4 |
| 298 | 99.99 | 16.4 | 0\5 | 93 | 11 |
| 301 | 100 | 23 | 1\5 | 58 | 8.8 |
| 302 | 99.51 | 13.4 | 0\5 | 87 | 13.4 |
| 305 | 99.91 | 12.2 | 0\5 | 87 | 9.6 |

TABLE 7-continued

| | 3 × 3 mg/kg | | | 3 × 1 mg/kg | |
|---|---|---|---|---|---|
| OZ | Activity (%) p.o. | Survival (days) SSV | Cures | Activity (%) p.o. | Survival (days) SSV |
| 306 | 99.75 | 7.6 | 0\5 | 85 | 11 |
| 309 | 99 | 9.2 | 0\5 | 66 | 9.4 |
| 315 | 99.99 | 22 | 0\5 | 81 | 12.2 |
| 317 | 100 | 16.8 | 0\5 | 73 | 11.4 |
| 319 | 99.97 | 11.2 | 0\5 | 92 | 13 |
| 320 | 96 | 9.6 | 0\5 | 50 | 8.6 |
| 323 | 99.95 | 14.4 | 0\5 | 66 | 14.4 |
| 329 | 100 | 27 | 2\5 | 99.86 | 11 |
| 330 | 99 | 12.6 | 0\5 | 45 | 9.2 |
| 333 | 99 | 10.2 | 0\5 | 64 | 9.4 |
| 335 | 99.99 | 15.4 | 0\5 | 98 | 10 |
| 336 | 100 | 20.8 | 0\5 | 99.14 | 10.4 |
| 337 | 99.98 | 14.4 | 0\5 | 96 | 9.4 |
| 338 | 100 | 25.6 | 0\5 | 98 | 9.4 |
| 339 | 100 | 27 | 3\5 | 97 | 9.2 |
| 343 | 100 | 22.2 | | 87 | 9.4 |
| 349 | 99.98 | 25.2 | 2\5 | 98 | 9.4 |
| 351 | 100 | 22.8 | | 99 | 9.6 |
| 343 | 100 | 22.2 | | 87 | 9.4 |
| 349 | 99.98 | 25.2 | 2\5 | 98 | 9.4 |
| 351 | 100 | 22.8 | | 99 | 9.6 |
| 353 | 99.99 | 16.4 | | 91 | 10 |
| 354 | 99.99 | 24.4 | | 95 | 8 |
| 357 | 100 | 22.4 | 1\5 | 98 | 9.2 |
| 358 | 99.98 | 9.8 | | 79 | 9.8 |
| 359 | 99.65 | 8.6 | | 79 | 8 |
| 365 | 99.96 | 12 | | 79 | 8.4 |
| 368 | 99.99 | 22.2 | | 91 | 8.6 |
| CQ | 99.54 | 10 | | 25 | 7.2 |
| MFQ | 98 | 12 | | 2 | 6.2 |
| AM | 86 | 9.4 | | 51 | 7.2 |
| AS | 78 | 9.4 | | 39 | 6.8 |

As shown by Table 7, at the 3×3 mg/kg dose, fourteen trioxolanes had activities of 100% and produced high survival numbers. Of these, OZ301, OZ329, OZ339, OZ349, and OZ357 cured 1/5, 2/5, 3/5, 2/5, and 1/5 of the infected mice, respectively. At the 3×1 mg/kg dose, most of the trioxolanes were more potent than the reference antimalarial drugs; sixteen of these had activities ≧90%. OZ209, OZ329, and OZ336 were the only trioxolanes with activities greater than 99% at the 3×1 mg/kg dose. All of OZ343-OZ368 that were tested were more active than the reference antimalarial drugs.

Prophylactic activities of the compounds were compared after administering po single dose of 100 mg/kg to different groups of five animals at various times before infection. All groups including an untreated control group, were then infected at the same time. Parasitemia was determined for each animal on day 3 post-infection, and percent of reduction of the level of parasitemia compared to levels for animals given no drug is determined. The results are shown in Table 8.

TABLE 8

| | Prophylactic Activity (%) | | | | | | | | | |
|---|---|---|---|---|---|---|---|---|---|---|
| | AM | AS | CQ | MFQ | 209 | 256 | 271 | 277 | 279 | 281 |
| 72 h - | | | | 99.97 | 99.92 | 13 | 99.89 | 9 | 14 | 8 |
| 48 h - | | | 57.49 | 99.92 | 99.9 | 29 | 99.98 | 7 | 27 | 45 |
| 24 h - | 0 | 6.28 | 99.92 | 100 | 100 | 82 | 100 | 25 | 97 | 99.23 |
| 0 h | 100 | 92.44 | 100 | 100 | 100 | 100 | 100 | 100 | 100 | 100 |

The unique prophylactic property of OZ209 (3-day protection, same as MFQ) was found also for OZ271.

EXAMPLE 6

Preferred Procedures for Preparation of OZ370-OZ405 cis-Adamantane-2-spiro-3'-8'-[2'-(1'H-tetrazol-5'-yl)ethyl]-1',2',4'-trioxaspiro[4.5]decane (OZ370). Step 1. A solution of the OZ352-HOSu active ester (0.6 g, 1.38 mmol) [for the preparation of the OZ352-HOSu active ester, see OZ353], and 3-aminopropionitrile (0.12 g, 1.66 mmol) in $CHCl_3$ (30 ml) under $N_2$ was stirred at rt for 24 h. After the reaction mixture was quenched with water (50 ml) at 0° C., the resulting solid was filtered, washed with 95% ethanol (10 ml), and dried to afford the amido nitrile (0.725 g, 100%) as a colorless solid. $^1$H NMR (500 MHz, $CDCl_3$) δ 1.14-1.37 (m, 4H), 1.53-2.07 (m, 21H), 2.22 (t, J=7.8 Hz, 2H), 2.63 (t, J=6.1 Hz, 2H), 3.49 (td, J=6.4, 6.1 Hz, 2H), 5.93 (brs, 1H). Step 2. To a solution of the nitrile (0.76 g, 1.88 mmol), triphenylphosphine (0.74 g, 2.82 mmol), and trimethylsilyl azide (0.325 g, 2.82 mmol) in THF (50 ml) at 0° C. under $N_2$ was added dropwise a solution of diethyl azodicarboxylate (0.60 g, 2.82 mmol) in THF (15 ml). The reaction mixture was slowly warmed to rt and stirred overnight. The reaction mixture was diluted with water (100 ml) and extracted with EtOAc (3×25 ml). The combined organic layers were washed with saturated aqueous $NaHCO_3$ (2×25 ml) and brine (30 ml) and dried over $MgSO_4$. After the solvents were removed, the residue was purified by chromatography (silica gel, 20% EtOAc in hexanes) to give the cyanoethyl protected tetrazole (0.65 g, 84%) as a colorless solid. $^1$H NMR (500 MHz, $CDCl_3$) δ1.16-1.46 (m, 4H), 1.90-1.99 (m, 14H), 1.67-1.83 (m, 7H), 2.91 (t, J=7.8 Hz, 2H), 3.01 (t, J=6.8 Hz, 2H), 4.54 (t, J=6.8 Hz, 2H). Step 3.

To the solution of NaOH (0.1 g, 2.36 mmol) in water (5 ml) was added dropwise a solution of the cyanoethyl protected tetrazole (0.65 g, 1.57 mmol) in THF (50 ml). After the reaction was stirred at rt for 3 h, the solvent was removed. The residue was diluted with saturated aqueous NaHCO$_3$ (50 ml) and washed with ether (2×25 ml). The aqueous phase was neutralized with 1 M aq. HCl and extracted with CH$_2$Cl$_2$ (3×25 ml). The combined organic layers were washed with water and brine, dried over MgSO$_4$, filtered, and concentrated to afford trioxolane OZ370 (0.35 g, 62%) as a colorless solid. mp 142-144° C.; $^1$H NMR (500 MHz, CDCl$_3$) δ1.18-1.29 (m, 2H), 1.34-1.46 (m, 1H), 1.62-2.01 (m, 22H), 3.12 (t, J=8.1 Hz, 2H); $^{13}$C NMR (125.7 MHz, CDCl$_3$) δ21.22, 26.44, 26.83, 29.62, 33.86, 33.90, 34.76, 35.39, 36.36, 36.75, 108.69, 111.40, 156.93. Anal Calcd for C$_{19}$H$_{28}$N$_4$O$_3$•0.8 H$_2$O: C, 60.88; H, 7.96; N, 14.95. Found: C, 60.60; H, 7.62; N, 14.71.

Adamantane-2-spiro-3'-5',5'-bis[4'-(aminomethyl)phenyl]-1',2',4'-trioxolane dimesylate (OZ371). Step 1. To a solution of OZ125 (1.0 g, 2.00 mmol) in ether (5 ml) and THF (2 ml) was added dropwise 2 M lithium borohydride in THF (2.00 ml, 4 mmol) followed by 1 M lithium triethylborohydride in THF (0.4 ml, 0.4 mmol). The resulting mixture was stirred at rt for 24 h and then diluted with ether (30 ml). The mixture was washed with 1 M aqueous NaOH (2×5 ml), water (2×5 ml), and brine (5 ml), dried over MgSO$_4$, filtered, and concentrated to afford the diol (0.80 g, 96%) as a colorless solid. Step 2. Diisopropyl azodicarboxylate (0.70 ml, 3.53 mmol) was added dropwise to a mixture of the diol (0.80 g, 1.96 mmol), phthalimide (0.57 g, 3.87 mmol), and triphenylphosphine (1.31 g, 5 mmol) in THF (20 ml) at 0° C. under N$_2$. The resulting mixture was stirred at rt for 24 h and then quenched with 5% aqueous NaHCO$_3$ (20 ml). The solid was collected by filtration and washed with water, THF, and ether to afford the phthalimido trioxolane (1.06 g, 81%) as a white solid. Step 3. A mixture of the phthalimido trioxolane (0.73 g, 1.10 mmol) and hydrazine monohydrate (1 ml) in chloroform (30 ml) and methanol (4 ml) was heated at 50° C. for 24 h. The reaction mixture was cooled to rt, filtered to remove the solid by-product, and concentrated. The residue was dissolved in CHCl$_3$, washed with brine, dried over MgSO$_4$, filtered, and treated with a solution of methanesulfonic acid (0.21 g) in CHCl$_3$ (10 ml). After removal of the solvent, the crude product was purified by crystallization from EtOH/CHCl$_3$ (1:4) to afford trioxolane OZ371 (0.20 g, 37%) as a colorless solid. mp 147-148° C.; $^1$H NMR (500 MHz, CD$_3$OD) δ1.62-1.94 (m, 12H), 2.18-2.25 (m, 2H), 2.68 (s, 6H), 4.13 (s, 4H), 7.47 (d, J=8.3 Hz, 4H), 7.57 (d, J=8.3 Hz, 4H); $^{13}$C NMR (125.7 MHz, CD$_3$OD) □ 27.85, 28.28, 35.70, 35.94, 37.59, 37.64, 39.48, 43.88, 110.22, 115.35, 128.61, 129.94, 135.26, 142.17. Anal. Calcd for C$_{27}$H$_{38}$N$_2$O$_9$S$_2$: C, 54.16; H, 6.40; N, 4.68. Found: C, 53.96; H, 6.29; N, 4.80.

cis-Adamantane-2-spiro-3'-8'-[(1'-piperidinylsulfonyl)methyl]-1',2',4'-trioxaspiro[4.5]decane (OZ372). Step 1. To a stirred solution of 4-(bromomethyl)cyclohexanone (1.5 g, 7.85 mmol) in acetone (20 ml) was added a solution of sodium sulfite (1.1 g, 8.73 mmol) in water (20 ml). The resulting mixture was refluxed for 24 h. After the mixture was evaporated to dryness, the solid residue was washed with CH$_2$Cl$_2$ (50 ml) and acetone (50 ml) and then dried in vacuo at 40° C. to afford the sodium sulfonate. Step 2. To a suspension of the sulfonate in CH$_3$CN (30 ml) was added 18-crown-6 (0.10 g) followed by cyanuric chloride (1.5 g, 8.15 mmol). The mixture was refluxed for 26 h and cooled to rt. After filtration through a Celite pad, the solvent was removed. The residue was purified by chromatography (silica gel, 20% EtOAc in hexanes) to afford the sulfonyl chloride (0.30 g, 18%). Step 3. To a solution of piperidine (0.50 g, 5.88 mmol) in CH$_2$Cl$_2$ (10 ml) at 0° C. was added a solution of the sulfonyl chloride (0.30 g, 1.43 mmol) in CH$_2$Cl$_2$ (10 ml). The resulting mixture was stirred at rt for 3 h and then quenched with water (20 ml). After separation of the organic layer, the aqueous layer was extracted with CH$_2$Cl$_2$ (2×20 ml). The combined extracts were washed with water (2×20 ml) and brine (20 ml), dried over MgSO$_4$, filtered, and concentrated to give an oil, which was purified by chromatography (silica gel, 15% EtOAc in hexanes) to afford the keto sulfonamide (0.25 g, 68%) as a white solid. $^1$H NMR (500 MHz, CDCl$_3$) δ1.47-1.68 (m, 8H), 2.25-2.49 (m, 7H), 2.79 (d, J=6.4 Hz, 2H), 3.19 (t, J=5.4 Hz, 4H). Step 4. A solution of O-methyl 2-adamantanone oxime (0.50 g, 2.8 mmol) and the keto sulfonamide (0.25 g, 0.97 mmol) in CH$_2$Cl$_2$ (15 ml) and cyclohexane (60 ml) was treated with ozone according to the general procedure. The crude product was purified by chromatography (silica gel, 10% EtOAc in hexanes) to afford trioxolane OZ372 (0.12 g, 29%) as a colorless solid. mp 120-124° C.; $^1$H NMR (500 MHz, CDCl$_3$) δ1.28-1.43 (m, 2H), 1.60-2.07 (m, 27H), 2.72 (d, J=5.9 Hz, 2H), 3.20 (t, J=5.6 Hz, 4H); $^{13}$C NMR (125.7 MHz, CDCl$_3$) δ23.77, 25.56, 26.45, 26.83 30.12, 31.62, 33.75, 34.77, 36.36, 36.76, 39.25, 46.57, 53.74, 108.00, 111.50. Anal. Calcd for C$_{22}$H$_{35}$NO$_5$S: C, 62.09; H, 8.29; N, 3.29. Found: C, 62.12; H, 8.09; N, 3.10.

cis-Adamantane-2-spiro-3'-8'-[[1'-(2'-amino-2'-methylpropyl)-1'H-tetrazol-5'-yl]methyl]-1',2',4'-trioxaspiro[4.5]decane (OZ373). To a mixture of OZ277 free base (0.46 g, 1.17 mmol), triphenylphosphine (0.77 g, 2.94 mmol), and trimethylsilyl azide (0.34 g, 2.95 mmol) in THF (20 ml) at 0° C. under N$_2$ was added dropwise diisopropyl azodicarboxylate (0.71 g, 3.51 mmol). The mixture was slowly warmed to rt and stirred for 72 h. The reaction mixture was diluted with water (50 ml) and extracted with EtOAc (2×50 ml). The combined extracts were washed with saturated aqueous NaHCO$_3$ (2×50 ml) and brine (50 ml), dried over MgSO$_4$, filtered, and concentrated. To a solution of the residue CHCl$_3$ (20 ml) was added a solution of p-toluenesulfonic acid monohydrate (0.22 g) in ethanol (10 ml). After evaporation of the solvents, the crude product was purified by crystallization from MeOH/CH$_2$Cl$_2$ (1:4) to afford trioxolane OZ373 (0.12 g, 17%) as a colorless solid. mp 220° C. dec; $^1$H NMR (500 MHz, CD$_3$OD) δ1.28-1.38 (m, 2H), 1.38 (s, 6H), 1.65-2.09 (m, 21H), 2.37 (s, 3H), 2.86 (d, J=6.8 Hz, 2H), 4.58 (s, 2H), 7.23 (d, J=7.8 Hz, 2H), 7.70 (d, J=7.8 Hz, 2H); $^{13}$C NMR (125.7 MHz, CD$_3$OD) δ21.30, 23.79, 27.97, 28.37, 30.04, 30.87, 34.87, 35.77, 35.78, 36.04, 37.80, 37.88, 54.02, 55.39, 109.53, 112.40, 126.97, 129.81, 141.66, 157.09.

cis-Adamantane-2-spiro-3'-8'-[4'-hydroxy-3'-(methoxymethyl)phenyl]-1',2',4'-trioxaspiro[4.5]decane (OZ374). Step 1. To a suspension of paraformaldehyde (0.61 g, 6.8 mmol), 4-(4-hydroxyphenyl)cyclohexanone (1.0 g, 5.26 mmol) in THF (30 ml) was added a solution of morpholine (0.60 g, 6.8 mmol) in THF (10 ml). The resulting suspension was stirred at 50° C. for 15 h. After removal of the solvent, the residue was extracted with CH$_2$Cl$_2$ (3×25 ml). The combined organic layers were washed with water and brine, dried over MgSO$_4$, filtered, and concentrated. The residue was purified by chromatography to afford 4-[4-hydoxy-3-(morpholinylmethyl)]cyclohexanone (0.91 g, 63%). $^1$H NMR (500 MHz, CDCl$_3$) δ1.84-1.93 (m, 2H), 2.16-2.20 (m, 2H), 2.46-2.57 (m, 8H), 2.91-2.95 (m, 1H), 3.69 (s, 2H), 3.70 (brs, 4H), 6.78 (d, J=8.3 Hz, 1H), 6.85 (d, J=2.0 Hz, 1H), 7.06 (dd, J=8.3, 2.4 Hz, 1H), 10.50 (brs, 1H). Step 2. A solution of 4-[4- hydoxy-3-(morpholinylmethyl)]cyclohexanone (0.81 g, 2.80 mmol) in acetic anhydride (10 ml) and acetic acid (0.5 ml) was refluxed for 24 h. The reaction mixture was concentrated, diluted with water (50 ml), and extracted with $CH_2Cl_2$ (3×25 ml). The combined organic layers were washed with water, aq. $NaHCO_3$, and brine, dried over $MgSO_4$, filtered, and concentrated to afford 4-[4-acetoxy-3-(acetoxymethyl)phenyl]cyclohexanone as a liquid. $^1$H NMR (500 MHz, $CDCl_3$) δ1.89-1.97 (m, 2H), 2.08 (s, 3H), 2.22-2.31 (m, 2H), 2.32 (s, 3H), 2.49-2.52 (m, 4H), 3.02-3.09 (m, 1H), 5.06 (s, 2H), 7.05 (d, J=8.3 Hz, 1H), 7.24 (dd, J=8.3, 2.4 Hz, 1H), 7.31 (d, J=2.4 Hz, 1H). Step 3. A solution of O-methyl 2-adamantanone oxime (1.29 g, 7.18 mmol) and 4-[4-acetoxy-3-(acetoxymethyl)phenyl]cyclohexanone (1.46 g, 4.79 mmol) in cyclohexane (90 ml) and $CH_2Cl_2$ (10 ml) was treated with ozone according to the general procedure. After removal of the solvents, the residue was purified by crystallization from 80% aqueous ethanol (50 ml) to afford cis-adamantane-2-spiro-3'-8'-[4'-acetoxy-3'-(acetoxymethyl)phenyl]-1',2',4'-trioxaspiro[4.5]decane (1.64 g, 73%) as a colorless solid. mp 123-125° C.; $^1$H NMR (500 MHz, $CDCl_3$) δ1.64-2.06 (m, 22H), 2.07 (s, 3H), 2.30 (s, 3H), 2.31-2.56 (m, 1H), 5.04 (s, 2H), 7.01 (d, J=8.3 Hz, 1H), 7.19 (dd, J=8.3, 2.0 Hz, 1H), 7.25 (d, J=2.0 Hz, 1H). Step 4. A mixture of the diacetate trioxolane (1.20 g, 2.56 mmol), water (2 ml), and KOH (0.57 g, 10.21 mmol) in methanol (25 ml) was heated at 50° C. for 1.5 h. After the solvent was removed, the residue was diluted with water (50 ml). The aqueous layer was carefully acidified with 1 M aq. HCl at 0° C. The solid was filtered, washed with EtOH, and recrystallized from EtOH to afford trioxolane OZ374 (0.78 g, 80%). mp 120-122° C.; $^1$H NMR (500 MHz, $CDCl_3$) δ1.62-2.09 (m, 22H), 2.40-2.51 (m, 1H), 3.44 (s, 3H), 4.62 (s, 2H), 6.80 (d, J=8.3 Hz, 1H), 6.85 (d, J=2.0 Hz, 1H), 7.04 (dd, J=8.3, 2.5 Hz, 1H), 7.29 (s, 1H); $^{13}$C NMR (125.7 MHz, $CDCl_3$) δ26.48, 26.88, 31.66, 34.71, 34.79, 36.39, 36.79, 42.00, 58.26, 74.28, 108.39, 111.36, 116.30, 121.77, 126.26, 127.71, 137.59, 154.41. Anal. Calcd for $C_{24}H_{32}O_5$: C, 71.97; H, 8.05. Found: C, 72.12; H, 7.99.

cis-Adamantane-2-spiro-3'-8'-[4'-[2'-[(aminoiminomethyl)amino]ethoxy]phenyl]-1',2',4'-trioxaspiro[4.5]decane hydrochloride (OZ375). A mixture of cis-adamantane-2-spiro-3'-8'-[4'-(2'-aminoethoxy)phenyl]-1',2',4'-trioxaspiro[4.5]decane (400 mg, 1 mmol), 1H-pyrazole-1-carboxamidine (147 mg, 1.0 mmol), N,N-diisopropylethylamine (129 mg, 1.0 mmol) in DMF (5 ml) was stirred at rt for 16 h and diluted with ether (50 ml). The solid was collected by filtration and crystallized from 30% aq. ethanol to afford trioxolane OZ375 (250 mg, 52%) as a colorless solid. mp 152-153° C.; $^1$H NMR (500 MHz, DMSO-$d_6$) δ1.45-1.61 (m, 2H), 1.62-2.01 (m, 20H), 2.50-2.62 (m, 1H), 3.49-3.54 (m, 2H), 4.02 (t, J=5.4Hz, 2H), 6.87 (d, J=8.7 Hz, 2H), 7.14 (d, J=8.7 Hz, 2H), 6.90-7.70 (m, 4H), 7.83 (s, 1H); $^{13}$C NMR (125.7 MHz, DMSO-$d_6$) δ25.99, 26.40, 31.47, 34.27, 34.44, 35.96, 36.26, 40.58, 40.87, 66.10, 108.31, 110.72, 114.68, 127.69, 138.63, 156.59, 157.44. Anal. Calcd for $C_{25}H_{36}ClN_3O_4$: C, 62.81; H, 7.59; N, 8.79. Found: C, 62.68; H, 7.70; N, 8.67.

cis-Adamantane-2-spiro-3'-8'-[4'-[2'-[(aminoethoxy)phenyl]-1',2',4'-trioxaspiro[4.5]decane hydrochloride (OZ376). To a solution of cis-adamantane-2-spiro-3'-8'-[4'-(2'-aminoethoxy)phenyl]-1',2',4'-trioxaspiro[4.5]decane (400 mg, 1.0 mmol) in $CH_2Cl_2$ (10 ml) was added 1 M HCl in ether (1 ml). After dilution with ether (10 ml), the resulting precipitate was collected by filtration and triturated with MeOH (4 ml) to afford trioxolane OZ376 (240 mg, 55%) as a colorless solid. mp 110° C. dec; $^1$H NMR (500 MHz, $CDCl_3$—$CD_3OD$) δ1.61-2.08 (m, 22H), 2.43-2.60 (m, 1H), 3.33 (s, 2H), 4.20 (s, 2H), 6.87 (d, J=8.3 Hz, 2H), 7.15 (d, J=8.3 Hz, 2H); $^{13}$C NMR (125.7 MHz, $CDCl_3$—$CD_3OD$) δ26.26, 26.65, 31.35, 34.43, 34.55, 36.20, 36.52, 39.07, 41.77, 63.64, 108.24, 111.32, 114.27, 127.60, 139.46, 155.88. Anal. Calcd for $C_{24}H_{34}ClNO_4$: C, 66.12; H, 7.86; N, 3.21. Found: C, 66.17; H, 8.00; N, 3.38.

cis-Adamantane-2-spiro-3'-8'-[4'-(2'-aminoethoxy)phenyl]-1',2',4'-trioxaspiro[4.5]decane maleate (OZ377). To a solution of cis-adamantane-2-spiro-3'-8'-[4'-(2'-aminoethoxy)phenyl]-1',2',4'-trioxaspiro[4.5]decane (400 mg, 1.0 mmol) in $CH_2Cl_2$ (5 ml) was added a solution of maleic acid (116 mg, 1.0 mmol) in MeOH (3 ml). After dilution with ether (40 ml), the resulting precipitate was collected by filtration to afford trioxolane OZ377 (460 mg, 89%) as a colorless solid. mp 133-135° C.; $^1$H NMR (500 MHz, DMSO-$d_6$) δ1.42-1.61 (m, 2H),1.62-2.07 (m, 20H), 2.52-2.63 (m, 1H), 3.20 (t, J=5.1 Hz, 2H), 4.12 (t, J=5.1 Hz, 2H), 6.02 (s, 2H), 6.91 (d, J=8.8 Hz, 2H), 7.16 (d, J=8.8 Hz, 2H), 7.91 (s, 3H); $^{13}$C NMR (125.7 MHz, DMSO-$d_6$) δ25.99, 26.40, 31.47, 34.27, 34.44, 35.96, 36.26, 38.62, 40.87, 64.55, 108.30, 110.74, 114.77, 127.73, 136.32, 138.92, 156.33, 167.37. Anal. Calcd for $C_{28}H_{37}NO_8$: C, 65.23; H, 7.23; N, 2.72. Found: C, 65.36; H, 7.22; N, 2.90.

cis-Adamantane-2-spiro-3'-8'-[4'-(2'-aminoethoxy)phenyl]-1',2',4'-trioxaspiro[4.5]decane citrate (OZ378). To a solution of cis-adamantane-2-spiro-3'-8'-[4'-(2'-aminoethoxy)phenyl]-1',2',4'-trioxaspiro[4.5]decane (400 mg, 1 mmol) in $CH_2Cl_2$ (5 ml) was added a solution of citric acid (190 mg, 1 mmol) in EtOH (3 ml). After concentration, the residue was triturated with $CH_2Cl_2$/ether(1:2, 15 ml) to afford trioxolane OZ378 (530 mg, 90%). mp 105° C. dec; $^1$H NMR (500 MHz, DMSO-$d_6$) δ1.42-1.60 (m, 2H), 1.61-2.05 (m, 20H), 2.50 (AB system, 4H), 2.52-2.63 (m, 1H), 2.90-3.15 (m, 2H), 3.75-4.05 (m, 3H), 6.85 (brs, 2H), 7.13 (brs, 2H), 8.40-10.40 (m, 5H); $^{13}$C NMR (125.7 MHz, DMSO-$d_6$) δ26.00, 26.40, 31.46, 34.27, 34.44, 35.97, 36.27, 38.35, 40.87, 44.75, 64.59, 71.29, 108.30, 110.73, 114.71, 127.68, 138.82, 156.30, 171.57, 177.41. Anal. Calcd for $C_{30}H_{41}NO_{11}$: C, 60.90; H, 6.98; N, 2.37. Found: C, 60.72; H, 7.03; N, 2.60.

cis-Adamantane-2-spiro-3'-8'-carboxymethyl-1',2',4'-trioxaspiro[4.5]decane sodium salt (OZ379). To a solution of OZ78 (5.0 g, 15.5 mmol) in EtOH (200 ml) was added dropwise a solution of NaOH (0.62 g, 15.5 mmol) in $H_2O$ (10 ml). The resulting mixture was stirred at rt for 0.5 h and then concentrated. The residue was crystallized from EtOH/Ether (1:3) to afford trioxolane OZ379 (5.12 g, 96%) as a colorless sold. mp 150-152° C.; $^1$H NMR (500 MHz, $D_2O$) δ1.15-1.22 (m, 2H), 1.68-2.06 (m, 21H), 2.08 (d, J=6.8 Hz, 2H); $^{13}$C NMR (125.7 MHz, $D_2O$) δ28.70, 29.02, 32.37, 36.35, 36.49, 36.97, 37.10, 38.59, 38.74, 47.26, 112.94, 115.83, 185.32.

trans, cis-5-Hydroxyadamantane-2-spiro-3'-8'-carboxymethyl-1',2',4'-trioxa-spiro[4.5]decane (OZ380). Step 1. A solution of O-methyl 5-acetoxy-2-adamantanone oxime (5.07 g, 21.0 mmol) and 4-(methoxycarbonylmethyl)cyclohexanone (4.05 g×93%=3.77 g, 22 mmol) in cyclohexane (300 ml) and $CH_2Cl_2$ (100 ml) was treated with ozone according to the general procedure. After removal of solvents, the crude product was purified by chromatography (10% ether in hexanes) to afford the acetate trioxolane (mixture of isomers, 2.52 g, 30%) as a colorless oil. Recrystallization from EtOH provided the major isomer (1.42 g, 17%) as a white solid. mp 95-96° C.; $^1$H NMR (500 MHz, $CDCl_3$) δ1.18-1.35 (m, 2H), 1.60-2.18 (m, 18H), 1.96 (s, 3H), 2.22 (d, J=7.3 Hz, 2H) 2.27 (d, J=9.8 Hz, 2H), 3.67 (s, 3H); $^{13}$C NMR (125.7 MHz, CDCl$_3$) δ22.51, 28.75, 29.85, 33.06, 33.35, 33.81, 38.20, 38.26, 40.03, 40.58, 51.47, 78.60, 108.90, 109.79, 170.21, 173.16. Step 2. To a solution of the major isomer (1.3 g, 3.3 mmol) in EtOH (10 ml) and THF (10 ml) was added a solution of NaOH (0.4 g, 10 mmol) in water (8 ml). The resulting mixture was stirred at 50° C. for 4 h. After removal of the solvents, the residue was diluted with water (10 ml) and extracted with CH$_2$Cl$_2$ (2×20 ml). The aqueous layer was acidified to pH=3 with 1 M aq. HCl. The precipitate was collected by filtration, washed with water, and dried in a vacuum oven at 40° C. to give trioxolane OZ380 (1.08 g, 96%) as a colorless solid. mp 162-163° C. $^1$H NMR (500 MHz, CDCl$_3$) δ1.01-1.17 (m, 2H), 1.43-2.07 (m, 20H), 2.11 (d, J=6.3 Hz, 2H), 4.46 (s, 1H), 12.05 (s, 1H); $^{13}$C NMR (125.7 MHz, CDCl$_3$) δ28.23, 29.59, 32.49, 33.34, 33.54, 37.79, 40.40, 41.91, 44.43, 65.49, 108.63, 110.05, 173.72.

trans, cis-5-Hydroxyadamantane-2-spiro-3'-8'-[[[(2'-amino-2'-methylpropyl)-amino]carbonyl]methyl]-1',2',4'-trioxaspiro[4.5]decane p-tosylate (OZ381). Step 1. A solution of OZ380 (0.78 g, 2.3 mmol), HOSu (0.32 g, 2.78 mmol), and EDCI (0.55 g, 2.87 mmol) in DMF (10 ml) was stirred at rt for 24 h. Under ice cooling, the reaction was quenched with water (30 ml). The precipitate was collected by filtration, washed with cold water, and dried in a vacuum oven at 40° C. to give the active ester (0.89 g, 89%) as a colorless solid. $^1$H NMR (500 MHz, CDCl$_3$) δ1.28-1.42 (m, 2H), 1.52-2.16 (m, 20H), 2.50 (d, J=7.0 Hz, 2H), 2.84 (s, 4H). Step 2. To a solution of 1,2-diamino-2-methylpropane (0.25 g, 2.84 mmol) in CHCl$_3$ (10 ml) was added dropwise a solution of the active ester (0.44 g, 1.01 mmol) in CHCl$_3$ (20 ml). The resulting mixture was stirred at rt for 1 h and then quenched with water (30 ml). After separation of the organic layer, the aqueous layer was extracted with CHCl$_3$ (2×20 ml). The combined extracts were washed with water (2×20 ml) and brine (20 ml), dried over MgSO$_4$, filtered, and concentrated. The residue was crystallized from EtOAc to afford OZ381 free base (0.33 g, 80%) as a colorless solid. mp 168-170° C. $^1$H NMR (500 MHz, DMSO-d$_6$) δ0.93 (s, 6H), 1.02-1.18 (m, 2H), 1.43-2.01 (m, 20H), 2.03 (d, J=7.3 Hz, 2H), 2.93 (d, J=5.9 Hz, 2H), 4.46 (s, 1H), 7.62 (t, J=6.0 Hz, 1H). To a solution of the free base (0.33 g, 0.80 mmol) in CHCl$_3$ (20 ml) was added a solution of p-toluenesulfonic acid monohydrate (0.15 g, 0.79 mmol) in ethanol (10 ml). After evaporation of the solvent, the crude product was purified by crystallization from EtOH/Et$_2$O (1:5) to afford trioxolane OZ381 (0.44 g, 94%) as a colorless solid. mp 200° C. dec; $^1$H NMR (500 MHz, DMSO-d$_6$) δ1.02-1.15 (m, 2H), 1.16 (s, 6H), 1.46-2.02 (m, 20H), 2.06 (d, J=6.8 Hz, 2H), 2.29 (s, 3H), 3.19 (d, J=5.8 Hz, 2H), 4.47 (s, 1H), 7.12 (d, J=7.8 Hz, 2H), 7.49 (d, J=7.8 Hz, 2H), 7.71 (brs, 3H), 8.04 (t, J=6.0 Hz, 1H); $^{13}$C NMR (125.7 MHz, DMSO-d$_6$) δ20.95, 23.49, 28.24, 29.69, 32.70, 33.35, 33.53, 37.80, 41.90, 41.97, 44.44, 46.03, 54.53, 65.49, 108.69, 110.08, 125.66, 128.24, 137.84, 145.80, 172.51. Anal. Calcd for C$_{29}$H$_{44}$N$_2$O$_8$S: C, 59.98; H, 7.64; N, 4.82. Found: C, 59.71; H, 7.48; N, 5.02.

cis-Adamantane-2-spiro-3'-8'-[4'-hydroxy-3'-(hydroxymethyl)phenyl]-1',2',4'-trioxaspiro[4.5]decane (OZ382). To a solution of cis-adamantane-2-spiro-3'-8'-[4'-acetoxy-3'-(acetoxymethyl)phenyl]-1',2',4'-trioxaspiro[4.5]decane (0.50 g, 1.06 mmol) [For the preparation of the trioxolane diacetate, see OZ374] in methanol (50 ml) at rt was added dropwise a solution of hydrazine monohydrate (0.112 g, 2.34 mmol) in methanol (5 ml). After addition, the reaction was stirred at 60° C. overnight. After removal of the solvent, the residue was dissolved in CH$_2$Cl$_2$ (50 ml), washed with water and brine, and dried over MgSO$_4$. Removal of the solvent followed by crystallization from CH$_2$Cl$_2$/EtOH (4:1) afforded trioxolane OZ382 as a colorless solid (0.350 g, 85%). mp 130-132° C. $^1$H NMR (500 MHz, CDCl$_3$) δ1.63-2.08 (m, 22H), 2.37 (brs, 1H), 2.42-2.49 (m, 1H), 4.81 (s, 2H), 6.80 (d, J=8.3 Hz, 1H), 6.87 (d, J=2.4 Hz, 1H), 7.03 (dd, J=8.3, 2.4 Hz, 1H), 7.14 (brs, 1H); $^{13}$C NMR (125.7 MHz, CDCl$_3$) δ26.46, 26.86, 31.65, 34.69, 34.78, 36.38, 36.78, 41.98, 64.72, 108.40, 111.42, 116.37, 124.48, 126.01, 127.66, 137.85, 154.23. Anal. Calcd for C$_{23}$H$_{30}$O$_5$: C, 71.48; H, 7.82. Found: C, 71.54; H, 7.68.

cis-Adamantane-2-spiro-3'-8'-[3'-[(acetylamino)methyl]-4'-hydroxyphenyl]-1', 2',4'-trioxaspiro[4.5]decane (OZ383). Step 1. To a solution of cis-adamantane-2-spiro-3'-8'-[4'-acetoxy-3'-(acetoxymethyl)phenyl]-1',2',4'-trioxaspiro[4.5]decane (0.50 g, 1.06 mmol) in dry DMF (20 ml) at rt under Ar was added portion-wise sodium azide (0.14 g, 2.12 mmol). The reaction mixture was heated to 60° C. overnight, then cooled to rt, poured onto ice-water (100 ml), and extracted with EtOAc (3×25 ml). The organic phase was washed with water and brine and dried over MgSO$_4$. Removal of the solvent followed by chromatography (silica gel, 20% EtOAc in hexanes) afforded the trioxolane azide as a colorless solid (0.35 g, 68%). mp 130-132° C.; $^1$H NMR (500 MHz, CDCl$_3$) δ1.65-2.08 (m, 22H), 2.33 (s, 3H), 2.53-2.62 (m, 1H), 4.26 (s, 2H), 7.04 (d, J=8.8 Hz, 1H), 7.19 (s, 1H), 7.20 (d, J=8.8 Hz, 1H); $^{13}$C NMR (125.7 MHz, CDCl$_3$) δ20.91, 26.45, 26.85, 31.40, 34.58, 34.77, 36.37, 36.76, 42.31, 50.21, 108.17, 111.44, 122.57, 127.24, 127.82, 128.43, 144.30, 147.13, 169.25. Step 2. To a solution of the trioxolane azide (0.50 g, 1.10 mmol) in THF (20 ml) was added triphenylphosphine (0.430 g, 1.65 mmol) followed by water (1 ml). The reaction mixture was stirred at rt overnight. After removal of the solvent, the residue was dissolved in CH$_2$Cl$_2$ (50 ml), washed with water and brine, and dried over MgSO$_4$. Removal of the solvent by chromatography (silica gel, 40% EtOAc in hexanes) afforded trioxolane OZ383 as a colorless solid (0.325 g, 69%). mp 137-139° C.; $^1$H NMR (500 MHz, CDCl$_3$) δ1.61-2.05 (m, 22H), 2.02 (s, 3H), 2.42-2.49 (m, 1H), 4.30 (d, J=6.3 Hz, 2H), 6.47 (t, J=6.1 Hz, 1H), 6.86 (d, J=8.3 Hz, 1H), 6.89 (d, J=2.4 Hz, 1H), 7.05 (dd, J=8.3, 2.4 Hz, 1H), 9.18 (s, 1H); $^{13}$C NMR (125.7 MHz, CDCl$_3$) δ22.76, 26.47, 26.86, 31.67, 34.70, 34.80, 36.40, 36.78, 40.78, 41.89, 108.38, 111.41, 117.81, 123.92, 128.54, 128.59, 137.53, 154.03, 172.67. Anal. Calcd for C$_{25}$H$_{33}$NO$_5$: C, 70.23; H, 7.78; N, 3.28. Found: C, 70.05; H, 7.61; N, 3.38.

3-tert-Butyl-11-phthalimidomethyl-7,14,15-trioxadispiro[5.1.5.2]pentadecane (OZ384). A solution of O-methyl 4-tert-butylcyclohexanone oxime (2.74 g, 15 mmol) and 4-phthalimidomethylcyclohexanone (2.57 g, 10 mmol) in cyclohexane (100 ml) and CH$_2$Cl$_2$ (100 ml) was treated with ozone according to the general procedure. The reaction mixture was concentrated, triturated with ethanol (50 ml), and filtered. The cake was purified by flash chromatography (silica gel, 10% EtOAc in hexanes) to afford trioxolane OZ384 (0.41 g, 10%) as a colorless solid. mp 175° C. dec; $^1$H NMR (500 MHz, CDCl$_3$) δ0.86 (s, 9H), 0.94-1.05 (m, 1H), 1.21-1.42 (m, 4H), 1.47-2.02 (m, 13H), 3.56 (d, J=7.3 Hz, 2H), 7.70-7.74 (m, 2H), 7.81-7.87 (m, 2H); $^{13}$C NMR (125.7 MHz, CDCl$_3$) δ24.50, 27.66, 27.81, 32.29, 33.43, 34.54, 35.59, 43.10, 47.23, 108.74, 108.89, 123.24, 132.00, 133.92, 168.53. Anal. Calcd for C$_{25}$H$_{33}$NO$_5$: C, 70.23; H, 7.78; N, 3.28. Found: C, 70.46; H, 7.90; N, 3.43.

3-Aminomethyl-11-tert-butyl-7,14,15-trioxadispiro[5.1.5.2]pentadecane mesylate (OZ385). A solution of OZ384 (280 mg, 0.65 mmol) and hydrazine monohydrate (180 mg, 3.9 mmol) in chloroform/ethanol (7:3, 10 ml) under $N_2$ was heated at 55° C. for 16 h. The reaction mixture was cooled to rt and filtered to remove solid by-products. The filtrate was diluted with chloroform (10 ml), and washed with water (10 ml) and brine (10 ml), dried over $MgSO_4$, filtered, and concentrated. The crude product was dissolved in $CH_2Cl_2$/ether (1:3, 8 ml) and methanesulfonic acid (70 mg, 0.73 mmol) in ether (4 ml) was added. The precipitate was collected by filtration to afford trioxolane OZ385 (165 mg, 65%) as a colorless solid. mp 132° C. dec; $^1$H NMR (500 MHz, $CDCl_3$) δ0.87 (s, 9H), 0.93-1.07 (m, 1H), 1.19-1.39 (m, 4H), 1.49-1.61 (m, 2H), 1.65-2.07 (m, 11H), 2.78 (s, 3H), 2.83 (t, J=6.8 Hz, 2H), 7.50 (s, 3H); $^{13}$C NMR (125.7 MHz, $CDCl_3$) δ24.49, 27.33, 27.67, 32.31, 33.24, 34.34, 34.54, 39.34, 44.80, 47.21, 108.33, 109.08.

3-tert-Butyl-11-phenyl-7,14,15-trioxadispiro[5.1.5.2] pentadecane (OZ386). A solution of O-methyl 4-tert-butyl-cyclohexanone oxime (1.83 g, 10 mmol) and 4-phenylcyclohexanone (1.74 g, 10 mmol) in cyclohexane (100 ml) and $CH_2Cl_2$ (100 ml) was treated with ozone according to the general procedure. The crude product was purified by flash chromatography (silica gel, 10% EtOAc in hexanes) and further by crystallization from ethanol to afford trioxolane OZ386 (3:2 mixture of two diastereomers, 0.60 g, 17%) as a colorless solid. mp 110-115° C.; $^1$H NMR (500 MHz, $CDCl_3$) □ 0.86 (s, 3.6 H), 0.88 (s, 5.4 H), 0.95-1.07 (m, 1H), 1.20-1.41 (m, 4H), 1.50-2.13 (m, 12H), 2.50-2.61 (m, 1H), 7.15-7.35 (m, 5H); $^{13}$C NMR (125.7 MHz, $CDCl_3$) □ 24.54, 24.69, 27.56, 27.69, 31.37, 31.42, 32.26, 32.31, 34.55, 34.57, 34.60, 34.65, 42.86, 42.92, 46.63, 47.26, 108.12, 108.61, 108.90, 108.92, 126.13, 126.16, 126.73, 126.76, 128.36, 128.38, 146.04, 146.11. Anal. Calcd for $C_{22}H_{32}O_3$: C, 76.70; H, 9.36. Found: C, 76.58; H, 9.49.

cis-Adamantane-2-spiro-3'-8'-[[(3'-amino-3'-oxopropyl)amino]methyl]-1',2',4'-trioxaspiro[4.5]decane p-tosylate (OZ387). A mixture of β-alaninamide hydrochloride (640 mg, 5.1 mmol), cis-adamantane-2-spiro-3'-8'-formyl-1',2',4'-trioxaspiro[4.5]decane (730 mg, 2.5 mmol), and $NaBH_3CN$ (310 mg, 5.0 mmol) in methanol (50 ml) was stirred at rt overnight and then concentrated. The crude product was partitioned between saturated aq. $NaHCO_3$ and $CHCl_3$. The $CHCl_3$ layer was washed with water and brine and concentrated. The residue was dissolved in $CH_2Cl_2$ (50 ml) and a solution of p-toluenesulfonic acid (300 mg) in methanol (3 ml) was added. After concentration, the crude product was triturated with $CHCl_3$ to afford trioxolane OZ387 (400 mg, 37%) as a colorless solid. mp 145-147° C.; $^1$H NMR (500 MHz, DMSO-$d_6$) δ1.05-1.22 (m, 2H), 1.59-2.03 (m, 21H), 2.29 (s, 3H), 2.83 (brs, 2H), 3.09 (brs, 2H), 3.30 (brs, 2H), 7.10 (s, 1H), 7.12 (d, J=7.8 Hz, 2H), 7.48 (d, J=7.8 Hz, 2H), 7.58 (s, 1H), 8.23 (s, 2H); $^{13}$C NMR (125.7 MHz, DMSO-$d_6$) δ20.95, 25.96, 26.37, 27.29, 30.54, 32.62, 32.96, 34.41, 34.43, 35.90, 36.23, 43.67, 51.71, 108.24, 110.84, 125.67, 128.22, 137.76, 145.93, 171.58.

cis-Adamantane-2-spiro-3'-8'-[3'-(aminomethyl)-4'-hydroxyphenyl]-1',2',4'-trioxaspiro[4.5]decane p-tosylate (OZ388). Step 1. To a solution of cis-adamantane-2-spiro-3'-8'-[4'-acetoxy-3'-(azidomethyl)phenyl]-1',2',4'-trioxaspiro[4.5]decane (0.20 g, 0.44 mmol) in methanol (20 ml) at rt was added dropwise a solution of hydrazine monohydrate (0.044 g, 0.88 mmol) in methanol (5 ml). After the reaction was stirred at rt overnight, the solvent was removed. The residue was dissolved in $CH_2Cl_2$ (50 ml), washed with water and brine, and dried over $MgSO_4$. Removal of the solvent followed by chromatography (silica gel, 20% EtOAc in hexanes) afforded the anticipated azido phenol as a colorless viscous liquid (0.140 g, 77%). $^1$H NMR (500 MHz, $CDCl_3$) δ1.70-2.06 (m, 22H), 2.44-2.53 (m, 1H), 4.38 (s, 2H), 5.76 (s, 1H), 6.77 (d, J=7.8 Hz, 1H), 7.04 (m, 2H). Step 2. To a solution of the azide (0.42 g, 1.02 mmol) in THF (20 ml) were added triphenylphosphine (0.268 g, 1.02 mmol) and water (1 ml). After the reaction mixture was stirred at rt overnight, the solvent was removed. The residue was dissolved in $CH_2Cl_2$ (50 ml), washed with water and brine, and dried over $MgSO_4$. Removal of the solvent followed by chromatography (silica gel, 40% EtOAC in hexanes) afforded the free base. To the solution of the free base (0.198 g, 0.514 mmol) in $CHCl_3$ (10 ml) was added a solution of p-toluenesulfonic acid monohydrate (0.088 g, 0.463 mmol) in EtOH (2 ml). After the reaction mixture was stirred for 1 h, the solvent was removed and ether was added. The precipitate was filtered, washed with ether, and dried to give trioxolane OZ388 (0.24 g, 81%) as a colorless solid. mp 150-152° C. $^1$H NMR (500 MHz, DMSO-$d_6$) δ1.48-1.59 (m, 2H), 1.62-1.96 (m, 20H), 2.29 (s, 3H), 2.46-2.55 (m, 1H), 3.93 (d, J=5.3 Hz, 2H), 6.82 (d, J=8.3 Hz, 1H), 7.04 (dd, J=8.3, 1.4 Hz, 1H), 7.12 (d, J=7.8 Hz, 2H), 7.16 (brs, 1H), 7.50 (d, J=7.8 Hz, 2H), 7.95 (brs, 3H), 9.90 (s, 1H); $^{13}$C NMR (125.7 MHz, DMSO-$d_6$) δ20.96, 26.01, 26.42, 31.47, 34.26, 34.44, 35.98, 36.27, 38.20, 40.89, 108.31, 110.73, 115.21, 119.90, 125.68, 128.20, 128.27, 128.45, 136.61, 137.90, 145.71, 153.95. Anal. Calcd for $C_{30}H_{39}NO_7S$: C, 64.61; H, 7.05; N, 2.51. Found: C, 64.71; H, 7.03; N, 2.54.

trans-Adamantane-2-spiro-3'-8'-hydroxymethyl-1',2',4'-trioxaspiro[4.5]decane (OZ389). A solution of trans-adamantane-2-spiro-3'-8'-ethoxycarbonyl-1',2',4'-trioxaspiro[4.5]decane (0.60 g, 1.78 mmol), lithium borohydride (0.90 ml, 1.8 mmol, 2 M in THF), and lithium triethylborohydride (0.20 ml, 0.20 mmol, 1 M in THF) in ether (10 ml) was stirred at rt for 3 h. The reaction mixture was diluted with ether (10 ml), washed with 3 M aq. NaOH (2×15 ml), water (2×15 ml), and brine (15 ml), dried over $MgSO_4$, filtered, and concentrated in vacuo. The crude product was purified by flash chromatography (silica gel, 20% EtOAc in hexanes) to afford trioxolane OZ389 (0.47 g, 90%) as a colorless solid. mp 55-56° C.; $^1$H NMR (500 MHz, $CDCl_3$) δ1.28-1.45 (m, 2H), 1.46-2.09 (m, 22H), 3.51 (d, J=6.3 Hz, 2H); $^{13}$C NMR (125.7 MHz, $CDCl_3$) δ26.39, 26.42, 26.84, 33,54, 34.67, 34.84, 36.31, 36.72, 39.02, 67.31, 108.82, 111.55. Anal. Calcd for $C_{17}H_{26}O_4$: C, 69.36; H, 8.90. Found: C, 69.55; H, 8.96.

cis-Adamantane-2-spiro-3'-8'-formyl-1',2',4'-trioxaspiro[4.5]decane (OZ390). To a solution of oxalyl chloride (8.45 g, 66.6 mmol) in $CH_2Cl_2$ (300 ml) at −78° C. was dropwise added DMSO (12.0 g, 153.6 mmol). After the reaction mixture was stirred for further 0.5 h, a solution of OZ119 (15.0 g, 51.1 mmol) in $CH_2Cl_2$ (50 ml) was added. The resulting mixture was stirred for 1 h before triethylamine (25.8 g, 255 mmol) was added and the stirring was continued for 0.5 h. After being warmed up to rt, the mixture was stirred for additional 1 h, then washed with water and brine, dried over $MgSO_4$, and concentrated to afford trioxolane OZ390 (14.8 g, 99%) as a colorless solid. mp 74-76° C. (50% ethanol); $^1$H NMR (500 MHz, $CDCl_3$) δ1.64-2.02 (m, 22 H), 2.20-2.30 (m, 1 H), 9.63 (d, J=1.1 Hz, 1H); $^{13}$C NMR (125.7 MHz, $CDCl_3$) δ23.24, 26.43, 26.84, 32.93, 33.20, 34.74, 34.80, 36.36, 36.74, 48.00, 107.89, 111.65, 203.55. Anal. Calcd for $C_{17}H_{24}O_4$: C, 69.84; H, 8.27. Found: C, 69.75; H, 8.14.

Adamantane-2-spiro-3'-8',8'-bis(ethoxycarbonyl)-1',2',4'-trioxaspiro[4.5]decane (OZ391). A solution of O-methyl 2-adamantanone oxime (4.19 g, 23.4 mmol) and 4,4-bis(ethoxycarbonyl)cyclohexanone (3.78 g, 15.6 mmol) in cyclohexane (270 ml) and $CH_2Cl_2$ (30 ml) was treated with ozone according to the general procedure. After removal of the solvents, the residue was purified by chromatography to afford trioxolane OZ391 (2.98 g, 47%). mp 70-72° C.; $^1$H NMR (500 MHz, CDCl$_3$) δ1.24 (t, J=7.3, 3H), 1.26 (t, J=7.3 Hz, 3H), 1.64-2.05 (m, 18H), 2.12-2.26 (m, 4H), 4.18 (q, J=6.8 Hz, 2H), 4.20 (q, J=6.8 Hz, 2H); $^{13}$C NMR (125.7 MHz, CDCl$_3$) δ13.99, 14.02, 26.43, 26.82, 28.81, 31.06, 34.72, 34.79, 36.32, 36.73, 53.72, 61.39, 61.40, 107.57, 111.71, 170.98, 171.12. Anal. Calcd for C$_{22}$H$_{32}$O$_7$: C, 64.69; H, 7.90. Found: C, 64.48; H, 7.68.

Adamantane-2-spiro-3'-8',8'-dicarboxy-1',2',4'-trioxaspiro[4.5]decane (OZ392). To a solution of OZ391 (1.0 g, 2.45 mmol) in 95% ethanol (50 ml) was added NaOH (0.490 g, 12.25 mmol) solution in water (2 ml). The mixture was stirred at 50° C. for 4 h, cooled to 0° C., and neutralized with 1 M aq. HCl. The precipitate was collected by filtration, washed with 50% aq. ethanol (25 ml), and dried to give trioxolane OZ392 (0.40 g, 46%) as a colorless solid. mp 149-151° C.; $^1$H NMR (500 MHz, DMSO-d$_6$) δ1.58-2.09 (m, 22H), 12.90 (s, 2H); $^{13}$C NMR (125.7 MHz, DMSO-d$_6$) δ25.99, 26.38, 28.79, 31.0, 34.41, 34.51, 35.90, 36.24, 53.02, 107.69, 111.14, 172.53, 172.61. Anal. Calcd for C$_{18}$H$_{24}$O$_7$: C, 61.35; H, 6.86. Found: C, 61.37; H, 7.06.

Adamantane-2-spiro-3'-8',8'-bis(hydroxymethyl)-1',2',4'-trioxaspiro[4.5]decane (OZ393). A mixture of OZ391 (1.85 g, 4.52 mmol), lithium borohydride (9.0 ml, 18.0 mmol, 2 M in THF), and lithiumtriethylborohydride (3.60 ml, 3.62 mmol, 1 M in THF) in ether (5 ml) was stirred at rt for 3 h. The mixture was diluted with ether (25 ml), washed with 3 M aq. NaOH (2×5 ml), water (3×5 ml), and brine (10 ml), dried over MgSO$_4$, filtered, and concentrated to afford trioxolane OZ393 (0.85 g, 58%) as a colorless solid. mp 142-144° C.; $^1$H NMR (500 MHz, CDCl$_3$) δ1.42-1.52 (m, 2H), 1.56-1.63 (m, 2H), 1.64-2.04 (m, 18H), 3.51 (d, J=5.4 Hz, 2H), 3.60 (d, J=5.4 Hz, 2H), 3.76-3.82 (m, 2H); $^{13}$C NMR (125.7 MHz, CDCl$_3$) δ26.22, 26.62, 26.73, 29.69, 34.52, 34.60, 36.14, 36.54, 37.43, 67.15, 68.83, 108.81, 111.18. Anal. Calcd for C$_{18}$H$_{28}$O$_5$: C, 66.64; H, 8.70. Found: C, 66.80; H, 8.63.

Adamantane-2-spiro-3'-7',7'-dimethyl-1',2',4'-trioxaspiro[4.5]decane (OZ394). A solution of O-methyl 2-adamantanone oxime (2.7 g, 15 mmol) and 3,3-dimethylcyclohexanone (1.26 g, 10 mmol) in cyclohexane (100 ml) and CH$_2$Cl$_2$ (20 ml) was treated with ozone according to the general procedure. After removal of solvents, the crude product was purified by chromatography (silica gel, hexanes) to afford trioxolane OZ394 (2.0 g, 68%) as a colorless oil. $^1$H NMR (500 MHz, CDCl$_3$) δ0.94 (s, 3H), 0.98 (s, 3H), 1.20-1.29 (m, 2H), 1.52-2.06 (m, 20H); $^{13}$C NMR (125.7 MHz, CDCl$_3$) δ19.87, 26.48, 26.89, 28.99, 30.00, 32.04, 34.53, 34.57, 34.66, 34.81, 35.15, 36.31, 36.40, 36.80, 38.38, 46.32, 109.36, 110.80. Anal. Calcd for C$_{18}$H$_{28}$O$_3$: C, 73.93; H, 9.65. Found: C, 74.12; H, 9.82.

trans-Adamantane-2-spiro-3'-8'-[[[(2'-amino-2'-methylpropyl)amino]carbonyl]methyl]-1',2',4'-trioxaspiro[4.5]decane p-tosylate (OZ395). Step 1. A solution of O-methyl 2-adamantanone oxime (15.82 g, 88.23 mmol) and 4-(methoxycarbonylmethyl)cyclohexanone (10.00 g, 58.82 mmol) in cyclohexane (400 ml) and CH$_2$Cl$_2$ (80 ml) was treated with ozone according to the general procedure. After removal of the solvents, the residue was purified by crystallization from 80% aq. ethanol (150 ml) to afford the cis-ester (8.109 g, 41%) as a colorless solid. Chromatography followed by repeated crystallizations from ethanol gave additional cis-trioxolane ester (2.12 g, 11%). Concentration of the mother liquor provided a 1:1 mixture of cis- and trans-esters (4.14 g, 21%) that was used for the next step.

Step 2. To a solution of cis- and trans-esters (4.1 g, 12.20 mmol) in 95% ethanol (50 ml) was added NaOH (1.46 g, 36.60 mmol) solution in water (10 ml). The mixture was stirred at 50° C. for 4 h, cooled to 0° C., and neutralized with 1.0 M aq. HCl. The precipitate was collected by filtration, washed with 50% aq. ethanol (50 ml), and dried in a vacuum oven at 40° C. to give 1:1 mixture of cis- and trans-acids (3.10 g, 77%) as a colorless solid. Step 3. A solution of 1:1 mixture of cis- and trans-acids (3.10 g, 9.62 mmol), HOBt (1.56 g, 11.55 mmol), and EDCI (2.28 g, 11.55 mmol) in DMF (50 ml) was stirred at 0° C. for 2 h before p-nitrophenol (1.6 g, 11.55 mmol) was added. After being stirred for a further 2 h at 0° C., the reaction mixture was stirred at rt overnight. The reaction mixture was quenched with ice-water (50 ml) at 0° C. and extracted with ethyl acetate (3×50 ml). The organic phase was washed with water (3×100 ml) and brine and dried over MgSO$_4$. After removal of the solvent, the residue was purified by chromatography followed by repeated crystallizations from ethanol to give pure trans p-nitrophenyl ester (0.210 g). $^1$H NMR (500 MHz, CDCl$_3$) δ1.51-2.05 (m, 23 H), 2.57 (d, J=6.84 Hz, 2H), 7.27 (d, J=9.3 Hz, 2H)), 8.27 (d, J=9.3 Hz, 2H). Step 4. To a solution of the trans p-nitrophenyl ester (0.180 g, 0.42 mmol) in CHCl$_3$ (5 ml) was rapidly added a solution of 1,2-diamino-2-methylpropane (0.184 g, 2.10 mmol) in CHCl$_3$ (5 ml). The reaction mixture was stirred at rt overnight and then quenched with water (15 ml). After separation of the organic layer, the aqueous layer was extracted with CHCl$_3$ (2×10 ml). The combined extracts were washed with water (3×25 ml), dried over MgSO$_4$, and concentrated to afford the trans free base (0.130 g, 80%) as a colorless solid. $^1$H NMR (500 MHz, CDCl$_3$) δ1.11 (s, 6H), 1.20 (brs, 2H), 1.34-1.44 (m, 2H), 1.58-2.03 (m, 21H), 2.15 (d, J=6.8 Hz, 2H), 3.14 (d, J=5.8 Hz, 2H), 6.02 (brs, 1H); $^{13}$C NMR (125.7 MHz, CDCl$_3$) δ26.43, 26.88, 28.74, 29.79, 33.75, 33.79, 34.69, 34.90, 36.32, 36.75, 43.46, 49.74, 50.22, 108.53, 111.52, 172.13. To a solution of the trans free base in CHCl$_3$ (5 ml) was added a solution of p-toluenesulfonic acid monohydrate (0.072 g, 0.38 mmol) in ethanol (1 ml). After removal of the solvent, the residue was treated with ether (15 ml). The precipitate was filtered, washed with ether (20 ml), and dried to afford trioxolane OZ395 (0.156 g, 85%) as a colorless solid. mp 150-152° C.; $^1$H NMR (500 MHz, CDCl$_3$) δ 1.17 (s, 6H), 1.21-1.34 (m, 2H), 1.51-1.98 (m, 21H), 2.10 (d, J=7.3 Hz, 2H), 2.29 (s, 3H), 3.20 (d, J=6.4 Hz, 2H), 7.12 (d, J=7.8 Hz, 2H), 7.48 (d, J=7.8 Hz, 2H), 7.71 (brs, 3H), 8.05 (t, J=6.3 Hz, 1H); $^{13}$C NMR (125.7 MHz, CDCl$_3$) δ 20.95, 23.48, 25.96, 26.37, 29.45, 32.85, 32.26, 34.38, 34.56, 35.93, 36.23, 41.71, 46.02, 54.53, 108.59, 110.92, 125.66, 128.24, 137.83, 145.81, 172.54.

Adamantane-2-spiro-3'-5'-[4'-[[(2'-amino-2'-methylpropyl)amino]carbonyl]phenyl]-5'-phenyl-1',2',4'-trioxolane p-tosylate (OZ396). Step 1. A solution of OZ139 (0.20 g, 0.50 mmol), HOSu (0.07 g, 0.60 mmol), and EDCI (0.12 g, 0.63 mmol) in DMF (15 ml) was stirred at rt for 24 h. Under ice cooling, the reaction was quenched with water (15 ml). The precipitate was collected by filtration, washed with cold water, and dried in a vacuum oven at 40° C. to give the active ester (0.2 g, 80%) as a colorless solid. $^1$H NMR (500 MHz, CDCl$_3$) δ1.64-2.02 (m, 12H), 2.16-2.26 (m, 2H), 2.91 (s, 4H), 7.32-7.38 (m, 3H), 7.41-7.46 (m, 2H), 7.70-7.76 (m, 2H), 8.12-8.18 (m, 2H). Step 2. To a solution of 1,2-diamino-2-methylpropane (0.10 g, 1.1 mmol) in CHCl$_3$ (10 ml) was added dropwise a solution of the active ester (0.20 g, 0.4 mmol) in CHCl$_3$ (10 ml). The resulting mixture was stirred at rt for 2 h and then quenched with water (10 ml). After separation of the organic layer, the aqueous layer was extracted with CHCl$_3$ (2×20 ml). The combined extracts were washed with water (2×10 ml) and brine (10 ml), dried over MgSO$_4$, filtered, and concentrated. The residue was dissolved in CH$_2$Cl$_2$ (2 ml) and then a solution of p-toluenesulfonic acid monohydrate (0.07 g) in ether (10 ml) was added. The precipitate was collected by filtration to afford trioxolane OZ396 (0.18 g, 69%) as a colorless solid. mp 137-139° C.; $^1$H NMR (500 MHz, DMSO-d$_6$) δ1.23 (s, 6H), 1.60-2.04 (m, 12H), 2.12 (d, J=11.7 Hz, 2H), 2.27 (s, 3H), 3.40 (d, J=5.9 Hz, 2H), 7.10 (d, J=7.8 Hz, 2H), 7.34-7.44 (m, 5H), 7.47 (d, J=7.8 Hz, 2H), 7.59 (d, J=7.3 Hz, 2H), 7.72 (brs, 3H), 7.91 (d, J=7.8 Hz, 2H), 8.72 (brs, 1H); $^{13}$C NMR (125.7 MHz, DMSO-d$_6$) δ20.94, 23.63, 25.90, 26.31, 34.32, 34.41, 34.80, 35.68, 35.87, 36.13, 46.76, 55.04, 109.00, 113.67, 125.66, 126.19, 126.74, 127.84, 128.21, 128.65, 129.46, 134.59, 137.75, 138.26, 143.57, 145.93, 167.32. Anal. Calcd for C$_{35}$H$_{42}$N$_2$O$_7$S: C, 66.22; H, 6.67; N, 4.41. Found: C, 66.24; H, 6.83; N, 4.37.

cis, cis-5-Hydroxyadamantane-2-spiro-3'-8'-[[[(2'-amino-2'-methylpropyl)-amino]carbonyl]methyl]-1',2',4'-trioxaspiro[4.5]decane p-tosylate (OZ397). Step 1. To a mixture of 5-hydroxy-2-admantanone (5.0 g, 30 mmol) in pyridine (20 ml) at 0° C. was added a solution of p-toluoyl chloride (10.0 g, 65 mmol) in pyridine (20 ml). The reaction mixture was stirred at 0° C. for 5 h and at rt for 18 h. After removal of the solvent, the residue was diluted with water (50 ml) and extracted with EtOAc (3×30 ml). The combined organic layers were washed with H$_2$O (2×20ml), dried over MgSO$_4$, and evaporated to dryness. The residue was purified by chromatography (silica gel, 0 to 15% ether in hexanes) to afford the 5-p-toluoyloxy-2-adamantanone (7.7 g, 90%) as a white powder. $^1$H NMR (500 MHz, CDCl$_3$) δ1.96-2.15 (m, 4H), 2.40 (s, 3H), 2.45-2.62 (m, 7H), 2.71 (s, 2H), 7.22 (d, J=8.3 Hz, 2H), 7.86 (d, J=8.3 Hz, 2H); $^{13}$C NMR (125.7 MHz, CDCl$_3$) δ21.57, 29.86, 38.18, 39.96, 41.35, 47.04, 77.91, 128.47, 128.93, 129.46, 143.40, 165.40, 215.55. Step 2. To a mixture of 5-p-toluoyloxy-2-adamantanone (7.7 g, 27.1 mmol) and pyridine (10 ml) in ethanol (40 ml) was added methoxylamine hydrochloride (2.5 g, 30 mmol). The mixture was stirred at rt for 48 h, concentrated, diluted with water (50 ml), and extracted with EtOAc (3×30 ml). The EtOAc layers were combined, dried over MgSO$_4$, and evaporated to dryness. The residue is purified by chromatography (silica gel, 10% ether in hexanes) to afford O-methyl 5-p-toluoyloxy-2-adamantanone oxime (8.0 g, 94%) as a white powder. $^1$H NMR (500 MHz, CDCl$_3$) δ1.73-1.99 (m, 4H), 2.23-2.51 (m, 7H), 2.40 (s, 3H), 2.78 (s, 1H), 3.69 (s, 1H), 3.83 (s, 3H), 7.21 (d, J=7.8 Hz, 2H), 7.85 (d, J=7.8 Hz, 2H); $^{13}$C NMR (125.7 MHz, CDCl$_3$) δ21.60, 30.39, 30.61, 36.39, 37.61, 37.85, 40.23, 40.53, 41.86, 61.10, 79.11, 128.81, 128.92, 129.47, 143.23, 163.60, 165.44. Step 3. A solution of O-methyl 5-p-toluoyloxy-2-adamantanone oxime (8.0 g, 25.5 mmol) and 4-(methoxycarbonylmethyl) cyclohexanone (7.5 g, 44 mmol) in cyclohexane (400 ml) and CH$_2$Cl$_2$ (100 ml) was treated with ozone according to the general procedure. After removal of the solvents, the crude product was purified by chromatography (silica gel, 0 to 20% ether in hexanes) to afford the trioxolane diester (mixture of four diastereomers, 6.5 g, 54%). Repeated chromatography (silica gel, 8% ether in hexanes) gave four fractions: isomers A+B (650 mg), isomer B (560 mg), isomers B+C (620 mg), and isomers C+D (550 mg). Crystallization of isomer B from acetone gave colorless single crystals. X-ray analysis established the configuration of isomer B as the trans, cis-diester. For isomer B: $^1$H NMR (500 MHz, CDCl$_3$) δ1.19-1.31 (m, 2H), 1.62-1.96 (m, 11H), 2.27-2.17 (m, 9H), 2.39 (s, 3H), 2.46 (d, J=11.7 Hz, 2H), 3.67 (s, 3H), 7.20 (d, J=7.8 Hz, 2H), 7.86 (d, J=7.8 Hz, 2H); $^{13}$C NMR (125.7 MHz, CDCl$_3$) δ21.58, 28.84, 29.84, 33.06, 33.42, 33.81, 38.28, 38.34, 40.30, 40.58, 51.46, 79.01, 108.93, 109.83, 128.87, 128.93, 129.43, 143.09, 165.49, 173.14. Repeated chromatography of the mixture of isomers B+C (silica gel, 8% ether in hexanes) gave isomer C (135 mg). The colorless single crystals obtained by crystallization from acetone were subjected to X-ray analysis that established the configuration of isomer C as the cis, cis-diester. $^1$H NMR (500 MHz, CDCl$_3$) δ1.21-1.33 (m, 2H), 1.65-2.03 (m, 11H), 2.17-2.33 (m, 11H), 2.39 (s, 3H), 3.67 (s, 3H), 7.20 (d, J=8.3 Hz, 2H), 7.85 (d, J=8.3 Hz, 2H); $^{13}$C NMR (125.7 MHz, CDCl$_3$) δ21.59, 29.22, 29.85, 33.09, 33.42, 33.75, 38.09, 38.44, 40.09, 40.57, 51.48, 78.59, 108.86, 109.87, 128.88, 128.96, 129.46, 143.10, 165.51, 173.18. Step 4. A mixture of the cis, cis-diester (95 mg, 0.202 mmol), EtOH (5 ml), THF (5 ml), and 1 M aq. NaOH (5 ml) was heated at 50 C for 18 h and then concentrated. The residue was dissolved in water (10 ml), washed with CH$_2$Cl$_2$ (3×5 ml), and acidified to pH=4 with 0.2 M aq. HCl. After the suspension was centrifuged, the supernatant was discarded. The solid pellet was dissolved in EtOH (3 ml) and the solution was centrifuged. The clear supernatant was collected, mixed with H$_2$O (3 ml) and kept at 4° C. for 48 h. The crystals were collected by means of centrifugation and freeze dried to give the cis, cis-acid (55 mg, 81%) as colorless needles. $^1$H NMR (500 MHz, DMSO-d$_6$) δ1.04-1.16 (m, 2H), 1.45-1.85 (m, 17H), 1.98 (brs, 3H), 2.11 (d, J=6.8 Hz, 2H), 4.48 (s, 1H), 12.04 (brs, 1H); $^{13}$C NMR (125.7 MHz, DMSO-d$_6$) δ28.63, 29.60, 32.52, 33.37, 33.47, 37.59, 40.42, 41.98, 44.51, 65.12, 108.62, 110.10, 173.76. Step 5. A solution of the cis, cis-acid (50 mg, 0.15 mmol), HOSu (25 mg, 0.22 mmol), and EDCI (50 mg, 0.26 mmol) in DMF (3 ml) was stirred at rt for 24 h. Under ice cooling, the reaction was quenched with water (15 ml). The precipitate was collected by filtration, washed with cold water, and dried in a vacuum oven at 40° C. to give the cis, cis-active ester (53 mg, 83%) as a colorless solid. $^1$H NMR (500 MHz, CDCl$_3$) δ1.34-1.46 (m, 2H), 1.56-2.06 (m, 17H), 2.14-2.21 (m, 3H), 2.56 (d, J=7.3 Hz, 2H), 2.88 (brs, 4H). Step 6. To a solution of 1,2-diamino-2-methylpropane (30 mg, 0.34 mmol) in CHCl$_3$ (10 ml) was added dropwise a solution of the cis, cis-active ester (53 mg, 0.12 mmol) in CHCl$_3$ (10 ml). The resulting mixture was stirred at rt for 3 h and then quenched with water (10 ml). After separation of the organic layer, the aqueous layer was extracted with CHCl$_3$ (2×20 ml). The combined extracts were washed with water (2×10 ml) and brine (10 ml), dried over MgSO$_4$, filtered, and concentrated. The residue was dissolved in CH$_2$Cl$_2$ (2 ml) and then a solution of p-toluenesulfonic acid monohydrate (19 mg) in ether (10 ml) was added. The precipitate was collected by filtration to afford trioxolane OZ397 (43 mg, 71%) as a colorless solid. mp 150-152 C; $^1$H NMR (500 MHz, DMSO-d$_6$) δ1.04-1.20 (m, 2H), 1.16 (s, 6H), 1.44-1.82 (m, 17H), 1.94-2.02 (m, 3H), 2.07 (d, J=7.3 Hz, 2H), 2.29 (s, 3H), 3.19 (d, J=5.8 Hz, 2H), 4.47 (brs, 1H), 7.11 (d, J=8.3 Hz, 2H), 7.47 (d, J=7.8 Hz, 2H), 7.67 (brs, 3H), 8.05 (t, J=6.0 Hz, 1H); $^{13}$C NMR (125.7 MHz, DMSO-d$_6$) δ20.94, 23.50, 28.61, 29.70, 33.35, 33.43, 37.58, 41.97, 44.50, 46.04, 54.54, 65.09, 108.65, 110.11, 125.66, 128.18, 137.66, 146.06, 172.55. Anal. Calcd for C$_{29}$H$_{44}$N$_2$O$_8$S: C, 59.98; H, 7.64; N, 4.82. Found: C, 59.97; H, 7.40; N, 4.93.

cis-Adamantane-2-spiro-3'-8'-[2'-(methoxycarbonyl) ethyl]-1',2',4'-trioxaspiro[4.5]decane (OZ398). See OZ352.

cis-Adamantane-2-spiro-3'-8'-[[[4'-(2'-hydroxyethyl)-1'-piperazinyl]carbonyl]methyl]-1',2',4'-trioxaspiro[4.5]decane (OZ399). To a solution of N-(2-hydroxyethyl)piperazine (325 mg, 2.5 mmol) in CHCl$_3$ (10 ml) was added the OZ78-HOBt active ester. The resulting mixture was stirred at rt for 2 h and then quenched with water (20 ml). After separation of the organic layer, the aqueous layer was extracted with CHCl$_3$ (2×20 ml). The combined extracts were washed with water (2×20 ml) and brine (20 ml), dried over MgSO$_4$, filtered, and concentrated. Crystallization of the residue from EtOAc gave trioxolane OZ399 (281 mg, 65%) as a colorless solid. mp 143-145° C.; $^1$H NMR (500 MHz, CDCl$_3$) δ1.26-1.31 (m, 2H), 1.62-2.04 (m, 21H), 2.21 (d, J=6.3 Hz, 2H), 2.44-2.54 (m, 4H), 2.56 (t, J=4.4 Hz, 2H), 2.62 (brs, 1H), 3.49 (t, J=4.0 Hz, 2H), 3.64 (t, J=4.4 Hz, 4H); $^{13}$C NMR (125.7 MHz, CDCl$_3$) δ26.43, 26.81, 30.25, 33.29, 34.02, 34.74, 36.34, 36.74, 39.10, 41.54, 45.71, 52.62, 53.15, 57.76, 59.25, 108.56, 111.28, 170.41.

4-Oxoadamantane-2-spiro-3'-1',2',4'-trioxaspiro[4.5]decane (OZ400). A solution of adamantane-2,4-dione (0.82 g, 5.0 mmol) and O-Methyl cyclohexanone oxime (0.32 g, 2.5 mmol) in cyclohexane (90 ml) and CH$_2$Cl$_2$ (10 ml) was treated with ozone according to the general procedure. After removal of the solvents, the residue was purified by chromatography to afford trioxolane OZ400 (5:1 mixture of two diastereomers, 0.690 g, 50%) as a colorless viscous liquid. $^1$H NMR (500 MHz, CDCl$_3$) δ1.32-1.49 (m, 2H), 1.52-2.26 (m, 17H), 2.28-2.42 (m, 1H), 2.48-2.58 (m, 1H), 2.72-2.79 (m, 1H); $^{13}$C NMR (125.7 MHz, CDCl$_3$) δ23.54, 23.64, 23.71, 24.71, 24.75, 25.80, 26.21, 31.30, 32.12, 33.61, 33.71, 34.03, 34.28, 34.39, 34.72, 35.54, 35.66, 37.44, 37.58, 38.69, 38.72, 44.96, 45.39, 55.64, 55.83, 110.02, 110.14, 111.07, 111.10, 212.50, 212.66. Anal. Calcd for C$_{16}$H$_{22}$O$_4$: C, 69.04; H, 7.97. Found: C, 69.22; H, 7.75.

cis-Adamantane-2-spiro-3'-8'-[4'-(3'-aminopropoxy)phenyl]-1',2',4'-trioxaspiro[4.5]decane mesylate (OZ401). To a solution of OZ288 (0.50 g, 1.4 mmol) in dry acetonitrile (30 ml) were added powdered NaOH (0.34 g, 8.43 mmol) and tetrabutylammonium hydrogensulfate (0.10 g, 0.28 mmol). The mixture was stirred at 25° C. for 30 min before 3-chloropropylamine hydrochloride (0.55 g, 4.21 mmol) was added. The reaction mixture was stirred at 60° C. overnight, cooled to rt, filtered, and washed with CH$_2$Cl$_2$. After the filtrate was concentrated, the residue was dissolved in CH$_2$Cl$_2$, washed with water and brine, and dried over MgSO$_4$. Removal of the solvent afforded the anticipated free base as a colorless solid (0.480 g, 83%). $^1$H NMR (500 MHz, CDCl$_3$) δ1.24 (brs, 2H), 1.65-2.04 (m, 24H), 2.46-2.51 (m, 1H), 2.89 (t, J=6.8 Hz, 2H), 4.02 (t, J=6.4 Hz, 2H), 6.82 (d, J=8.3 Hz, 2H), 7.10 (d, J=8.3 Hz, 2H). To the solution of the free base (0.480 g, 1.16 mmol) in CHCl$_3$ (10 ml) at 0° C. was added dropwise a solution of mehanesulfonic acid (0.10 g, 1.05 mmol) in ether (10 ml). The precipitate was filtered, washed with ether (25 ml), and dried to afford trioxolane OZ401 as a colorless solid (0.510 g, 86%). mp 158-160° C.; $^1$H NMR (500 MHz, DMSO-d$_6$) δ1.49-1.58 (m, 2H), 1.63-2.03 (m, 22H), 2.34 (s, 3H), 2.52-2.59 (m, 1H), 2.91-2.99 (m, 2H), 4.02 (t, J=5.9 Hz, 2H), 6.85 (d, J=8.3 Hz, 2H), 7.13 (d, J=8.8 Hz, 2H), 7.75 (brs, 3H); $^{13}$C NMR (125.7 MHz, DMSO-d$_6$) δ25.99, 26.40, 27.03, 31.49, 34.27, 34.44, 35.97, 36.27, 36.59, 39.92, 40.87, 64.62, 108.31, 110.72, 114.56, 127.61, 138.34, 156.75. Anal. Calcd for C$_{26}$H$_{39}$NO$_7$S: C, 61.27; H, 7.71; N, 2.75. Found: C, 61.08; H, 7.58; N, 2.59.

6-Oxoadamantane-2-spiro-3'-1',2',4'-trioxaspiro[4.5]decane (OZ402). A solution of adamantane-2,6-dione (0.33 g, 2.0 mmol) and O-methyl cyclohexanone oxime (0.13 g, 1.0 mmol) in cyclohexane (90 ml) and CH$_2$Cl$_2$ (10 ml) was treated with ozone according to the general procedure. After removal of the solvents, the residue was purified by chromatography to afford trioxolane OZ402 (0.245 g, 88%) as a colorless solid. mp 25-26° C.; $^1$H NMR (500 MHz, CDCl$_3$) δ1.32-1.48 (m, 2H), 1.52-1.81 (m, 8H), 1.86-1.99 (m, 4H), 2.10 (brs, 2H), 2.19-2.26 (m, 2H), 2.30-2.37 (m, 2H), 2.40-2.49 (m, 2H); $^{13}$C NMR (125.7 MHz, CDCl$_3$) δ23.79, 24.85, 34.62, 35.64, 35.68, 35.91, 44.70, 45.13, 108.89, 109.75, 215.96. Anal. Calcd for C$_{16}$H$_{22}$O$_4$: C, 69.04; H, 7.97. Found: C, 69.02; H, 7.75.

Adamantane-2-spiro-3'-5'-methyl-5'-phenyl-1',2',4'-trioxolane (OZ403). A solution of O-methyl 2-adamantanone oxime (2.7 g, 15 mmol) and acetophenone (1.2 g, 10 mmol) in cyclohexane (40 ml) and CH$_2$Cl$_2$ (30 ml) was treated with ozone according to the general procedure. After removal of solvents, the crude product was purified by chromatography (silica gel, 5% EtOAc in hexanes) to afford trioxolane OZ403 (1.05 g, 37%) as a white solid. mp 70-72° C.; $^1$H NMR (500 MHz, CDCl$_3$) δ1.72 (s, 3H), 1.56-2.20 (m, 14H), 7.28-7.38 (m, 3H), 7.50-7.56 (m, 2H); $^{13}$C NMR (125.7 MHz, CDCl$_3$) δ25.89, 26.45, 26.89, 34.53, 34.75, 34.78, 35.32, 35.39, 36.60, 36.79, 108.70, 112.90, 125.21, 128.06, 128.11, 142.55. Anal. Calcd for C$_{18}$H$_{22}$O$_3$: C, 75.50; H, 7.74. Found: C, 75.58; H, 7.63.

Adamantane-2-spiro-3'-5'-phenyl-1',2',4'-trioxolane (OZ404). Step 1. To a solution of benzaldehyde (5.0 g, 47 mmol) in ethanol (50 ml) was added pyridine (8 ml) followed by methoxylamine hydrochloride (4.0 g, 48 mmol). The reaction mixture was stirred at rt for 48 h, concentrated in vacuo, and diluted with CH$_2$Cl$_2$ (50 ml) and water (50 ml). After separation of the organic layer, the aqueous layer was extracted with CH$_2$Cl$_2$ (50 ml). The combined organic extracts were washed with 1 M aq. HCl (2×30 ml), saturated aq. NaHCO$_3$ (2×30 ml), and brine (30 ml), and dried over MgSO$_4$. Evaporation in vacuo afforded O-methyl benzaldehyde oxime (5.6 g, 88%) as a light yellow oil. [Konakahara, T.; Matsuki, M.; Sugimoto, S.; Sato, K. J. Chem. Soc., Perkin Trans. 1 1987, 1489-1493.] $^1$H NMR (500 MHz, CDCl$_3$) □3.98 (s, 3H), 7.35-7.42 (m, 3H), 7.56-7.62 (m, 2H), 8.06 (s, 1H). Step 2. A solution of O-methyl benzaldehyde oxime (1.35 g, 10 mmol) and 2-adamantanone (3.0 g, 20 mmol) in cyclohexane (90 ml) and CH$_2$Cl$_2$ (30 ml) was treated with ozone according to the general procedure. After removal of the solvents, the crude product was purified by chromatography (silica gel, 5% EtOAc in hexanes) to afford trioxolane OZ404 (0.35 g, 13%) as a colorless oil. $^1$H NMR (500 MHz, CDCl$_3$) δ1.70-1.93 (m, 9H), 2.03-2.16 (m, 4H), 2.22-2.26 (m, 1H), 6.09 (s, 1H), 7.36-7.46 (m, 3H), 7.50-7.56 (m, 2H); $^{13}$C NMR (125.7 MHz, CDCl$_3$) δ26.54, 26.83, 34.20, 34.61, 34.86, 35.66, 35.78, 36.78, 36.80, 103.66, 113.00, 127.85, 128.53, 130.31, 132.83. Anal. Calcd for C$_{17}$H$_{20}$O$_3$: C, 74.97; H, 7.40. Found: C, 74.94; H, 7.19.

Adamantane-2-spiro-3'-5'-phenyl-5'-[4'-(1'-piperazinylcarbonyl)phenyl]-1',2',4'-trioxolane p-tosylate (OZ405). To a solution of piperazine (0.10 g, 1.1 mmol) in CHCl$_3$ (10 ml) was added dropwise a solution of the corresponding active ester (0.20 g, 0.40 mmol) [see OZ396] in CHCl$_3$ (10 ml). The resulting mixture was stirred at rt for 2 h and then quenched with water (10 ml). After separation of the organic layer, the aqueous layer was extracted with CHCl$_3$ (2×20 ml). The combined extracts were washed with water (2×10 ml) and brine (10 ml), dried over MgSO$_4$, filtered, and concentrated. The residue was dissolved in CH$_2$Cl$_2$ (2 ml) and then a solution of p-toluenesulfonic acid monohydrate (0.07 g) in ether (10 ml) was added. The precipitate was collected by filtration to afford trioxolane OZ405 (0.24 g, 92%) as a colorless solid. mp 141-142° C.; $^1$H NMR (500 MHz, CDCl$_3$) δ1.62-1.94 (m, 12H), 2.06-2.16 (m, 2H), 2.28 (s, 3H), 3.14 (brs, 4H), 3.55 (brs, 4H), 7.11 (d, J=7.8 Hz, 2H), 7.35-7.56 (m, 11H), 8.78 (brs, 2H); $^{13}$C NMR (125.7 MHz, CDCl$_3$) δ20.94, 25.91, 26.32, 34.35, 34.42, 34.66, 35.71, 35.74, 36.12, 42.86, 108.94, 113.68, 125.66, 126.52, 126.63, 127.48, 128.24, 128.63, 129.25, 135.43, 137.83, 139.03, 141.44, 145.81, 168.83. Anal. Calcd for C$_{35}$H$_{40}$N$_2$O$_7$S: C, 66.43; H, 6.37; N, 4.43. Found: C, 66.55; H, 6.29; N, 4.24.

It should be appreciated that the spiro and dispiro 1,2,4-trioxolane compositions of this invention may contain trioxolanes within the scope of the formulas described above, or prodrugs or analogues of these compounds or a racemic mixture of either the D or the L form. The invention is also intended to include all biologically active salt forms of the compounds. Also, minor dosage and formulation modifications of the composition and the ranges expressed herein may be made and still come within the scope and spirit of the present invention.

Having described the invention with reference to particular compositions, theories of effectiveness, and the like, it will be apparent to those of skill in the art that it is not intended that the invention be limited by such illustrative embodiments or mechanisms, and that modifications can be made without departing from the scope or spirit of the invention, as defined by the appended claims. It is intended that all such obvious modifications and variations be included within the scope of the present invention as defined in the appended claims. The claims are meant to cover the claimed components and steps in any sequence which is effective to meet the objectives there intended, unless the context specifically indicates to the contrary.

What is claimed is:

1. A spiro or dispiro 1,2,4-trioxolane, wherein the spiro or dispiro 1,2,4-trioxolane is selected from the group consisting of: cis-Adamantane-2-spiro-3'-8'-[2'-(1'H-tetrazol-5'-yl)ethyl]-1',2',4'-trioxaspiro[4.5]decane, cis-Adamantane-2-spiro-3'-8'-[(1'-piperidinylsulfonyl)methyl]-1',2',4'trioxaspiro[4.5]decane, cis-Adamantane-2-spiro-3'-8'-[[1'-(2'-amino-2'-methylpropyl)-1'H-tetrazol-5'-yl]methyl]-1',2',4'-trioxaspiro[4.5]decane, cis-Adamantane-2-spiro-3'-8'-[4'-hydroxy-3'-(methoxymethyl)phenyl]-1',2',4'-trioxaspiro[4.5]decane, cis-Adamantane-2-spiro-3'-8'-[4'-[2'-[(aminoiminomethyl)amino]ethoxy]phenyl]-1',2',4'-trioxaspiro[4.5]decane hydrochloride, cis-Adamantane-2-spiro-3'-8'-[4'-(2'-aminoethoxy)phenyl]-1',2',4'-trioxaspiro[4.5]decane hydrochloride, cis-Adamantane-2-spiro-3'-8'-[4'-(2'-aminomethoxy)phenyl]-1',2',4'-trioxaspiro[4.5]decane maleate, cis-Adamantane-2-spiro-3'-8'-[4'-(2'-aminoethoxy)phenyl]-1',2',4'-trioxaspiro[4.5]decane citrate, cis-Adamantane-2-spiro-3'-8'-carboxymethyl-1',2',4'-trioxaspiro[4.5]decane sodium salt, trans, cis-5-Hydroxyadamantane-2-spiro-3'-8'-carboxymethyl-1',2',4'-trioxa-spiro[4.5]decane, trans, cis-5-Hydroxyadamantane-2-spiro-3'-8'-[[[(2'-amino-2'-methylpropyl)-amino]carbonyl]methyl]-1',2',4'-trioxaspiro[4.5]decane p-tosylate, cis-Adamantane-2-spiro-3'-8'-[4'-hydroxy-3'-(hydroxymethyl)phenyl]-1',2',4'-trioxaspiro[4.5]decane, cis-Adamantane-2-spiro-3'-8'-[3'-[(acetylamino)methyl]-4'-hydroxyphenyl]-1',2',4'-trioxaspiro[4.5]decane, cis-Adaniantane-2-spiro-3'-8'-[[(3'-amino-3'-oxopropyl)amnino]methyl]-1',2',4'-trioxaspiro[4.5]decane p-tosylate, cis-Adamantane-2-spiro-3'-8'-[3'-(aminomethyl)-4'-hydroxyphenyl]-1',2',4'-trioxaspiro[4.5]decane p-tosylate, trans-Adamantane-2-spiro-3'-8'-hydroxymethy-1',2',4'-trioxaspiro[4.5]decane, cis-Adamantane-2-spiro-3'-8'-formyl-1',2',4'-trioxaspiro[4.5]decane, Adamantane-2-spiro-3'-8',8'-bis(ethoxycrbonyl)-1',2',4'-trioxaspiro[4.5]de-cane, Adamantane-2-spiro-3'-8',8'-dicarboxy-1',2',4'-trioxaspiro[4.5]decane, Adamantane-2-spiro-3'-8',8'-bis(hydroxymethyl)-1',2',4'-trioxaspiro[4.5]decane, Adamantane-2-spiro-3'-7',7'-dimethyl-1',2',4'-trioxaspiro[4.5]decane, trans-Adamantane-2-spiro-3'-8'-[[[(2'-amino-2'-methylpropyl)amino]carbonyl]methyl]-1',2',4'-trioxaspiro[4.5]decane p-tosylate, cis,cis-5-Hydroxyadamantane-2-spiro-3'-8'-[[[(2'-amino-2'-methylpropyl)-amino]carbonyl]methyl]-1',2',4'-trioxaspiro[4.5]decane p-tosylate, cis-Adaxnantane-2-spiro-3'-8'-[2'-(methoxycarbonyl)ethyl]-1',2',4'-trioxaspiro[4.5]decane, cis-Adamantane-2-spiro-3'-8'-[[[4'-(2'-hydroxyethyl)-1'-piperazinyl]carbonyl]methyl]-1',2',4'-trioxaspiro[4.5]decane, 4-Oxoadamantane-2-spiro-3'-1',2',4'-trioxaspiro[4.5]decane, cis-Adamantane-2-spiro-3'-8'-[4'-(3'-aminopropoxy)phenyl]-1',2',4'-trioxaspiro[4.5]decane mesylate, and 6-Oxoadamantane-2-spiro-3'-1',2',4'-trioxaspiro[4.5]decane.

2. The spiro or dispiro 1,2,4-trioxolane of claim 1 that is selected from the group consisting of cis-Adamantane-2-spiro-3'-8'-[4'-(2'-aminoethoxy)phenyl]-1'2',4'-trioxaspirol[4.5]decane hydrochloride, cis-Adamantane-2-spiro-3'-8'-(4'-(2'-aminoethoxy)phenyl]-1',2',4'-trioxaspiro[4.5]decane maleate, cis-Adamantane-2-spiro-3'-8'-[4'-(2'-aminoethoxy)phenyl]-1',2',4'-trioxaspiro[4.5]decane citrate, cis-Adamantane-2-spiro-3'-8'-[[(3'-amino-3'-oxopropyl)amino]methyl]-1',2',4'-trioxaspiro[4.5]decane p-tosylate, cis-Adamantane-2-spiro-3'-8'-[3'-(aminomethyl)-4'-Hydroxyphenyl]-1',2',4'-trioxaspiro[4.5]decane p-tosylate, cis-Adamantane-2-spiro-3'-8'-[[[4'-(2'-hydroxyethyl)-1'-piperazinyl]carbonyl]methyl]-1',2',4'-trioxaspiro[4.5]decane, and cis-Adamantane-2-spiro-3'-8'-[4'-(3'-aminopropoxy)phenyl]-1',2',4'-trioxaspiro[4.5]decane mesylate.

3. The spiro or dispiro 1,2,4-trioxolane of claim 1 that is selected from the group consisting of cis-Adamantane-2-spiro-3'-8'-[4'-(2'-aminoethoxy)phenyl]-1',2',4'-trioxaspiro[4.5]decane hydrochloride, cis-Adamantane-2-spiro-3'-8'-[4'-(2'-aminoethoxy)phenyl]-1',2',4'-trioxaspiro[4.5]decane maleate, cis-Adamantane-2-spiro-3'-8'-[4'-(2'-aminoethoxy)phenyl]-1',2',4'-trioxaspiro[4.5]decane citrate, cis-Adamantane-2-spiro-3'-8'-[[(3'-amino-3'-oxopropyl)amino]methyl]-1',2',4'-trioxaspiro[4.5]decane p-tosylate, and cis-Adamantane-2-spiro-3'-8'-[4'-(3'-aminoethoxy)phenyl]-1',2',4'-trioxaspiro[4.5]decane mesylate.

4. A pharmaceutical composition comprising: an amount of a spiro or dispiro 1,2,4-trioxolane effective in inhibiting malarial infection or effective for treating malaria, said trioxolane selected from the group consisting of cis-Adamantane-2-spiro-3'-8'-[2'-(1'H-tetrazol-5'-yl)ethyl]-1',2',4'-trioxaspiro[4.5]decane, cis-Adamantane-2-spiro-3'-8'-[(1'-piperidinylsulfonyl)methyl]-1',2',4'-trioxaspiro[4.5]decane, cis-Adamantane-2-spiro-3'-8'-[[1'-(2'-amino-2'-methylpropyl)-1'H-tetrazol-5'-yl]methyl]-1',2',4'-trioxaspiro[4.5]decane, cis-Adamantane-2-spiro-3'-8'-[4'-hydroxy-3'-(methoxymethyl)phenyl]-1',2',4'-trioxaspiro[4.5]decane, cis-Adamantane-2-spiro-3'-8'-[4'-[2'-[(aminoiminomethyl)amino]ethoxy]phenyl]-1',2',4'-trioxaspiro[4.5]decane hydrochloride, cis-Adamantane-2-spiro-3'-8'-[4'-(2'-aminoethoxy)phenyl]-1',2',4'-trioxaspiro[4.5]decane hydrochloride, cis-Adamantane-2-spiro-3'-8'-[4'-(2'-aminoethoxy)phenyl]-1',2',4'-trioxaspiro[4.5]decane maleate, cis-Adamantane-2-spiro-3'-8'-[4'-(2'-aminoethoxy)phenyl]-1',2',4'-trioxaspiro[4.5]decane citrate, cis-Adamantane-2-spiro-3'-8'-carboxymethyl-1',2',4'-trioxaspiro[4.5]decane sodium salt, trans, cis-5-Hydroxyadamantane-2-spiro-3'-8'-carboxymethyl-1',2',4'-trioxa-spiro[4.5]decane, trans, cis-5-Hydroxyadamantane-2-spiro-3'-8'-[[[(2'-amino-2'-methyl-proply)-amino]carbonyl]methyl]-1',2',4'-trioxaspiro[4.5]decane p-tosylate, cis-Adamantane-2-spiro-3'-8'-[4'-hydroxy-3'-(hydroxymethyl)phenyl]-1',2',4'-trioxaspiro[4.5]

decane, cis-Adamantane-2-spiro-3'-8'-[3'-[(acetylamino)methyl]-4'-hydroxyphenyl]-1',2',4'-trioxaspiro[4.5]decane, cis-Adamantane-2-spiro-3'-8'-[[(3'-amino-3'-oxypropyl)amino]methyl]-1',2',4'-trioxaspiro[4.5]decane p-tosylate, cis-Adamantane-2-spiro-3'-8'-[3'-(aminomethyl)-4'-hydroxyphenyl]-1',2',4'-trioxaspiro[4.5]decane p-tosylate, trans-Adamantane-2-spiro-3'-8'-hydroxymethyl-1',2',4'-trioxaspiro[4.5]decane, cis-Adamantane-2-spiro-3'-8'-formyl-1',2',4'-trioxaspiro[4.5]decane, Adamantane-2-spiro-3'-8',8'-bis(ethoxycarbonyl)-1',2',4'-trioxaspiro[4.5]de-cane, Adamantane-2-spiro-3'-8',8'-dicarboxy-1',2',4'-trioxaspiro[4.5]decane, Adamantane-2-spiro-3'-8',8'-bis(hydromethyl)-1',2',4'-trioxaspiro[4.5]de-cane, Adamantane-2spiro-3'-7',7'-dimethyl-1',2',4'-trioxaspiro[4.5]decane, trans-Adamantane-2-spiro-3'-8'-[[[(2'-amino-2'-methylpropyl)animo]carbonyl]methyl]-1',2',4'-trioxaspiro[4.5]decane p-tosylate, cis, cis-5-Hydroxyadamantane-2-spiro-3'-8'-[[[(2'-amino-2'-methylpropyl)-amino]carbonyl]methyl]-1',2',4'-trioxaspiro[4.5]decane p-tosylate, cis-Adamantane-2-spiro-3'-8'-[2'-(methoxycarbonyl)ethyl]-1',2',4'-trioxaspiro[4.5]decane, cis-Adamantane-2-spiro-3'-8'-[[[4'-(2'-hydroxyethyl)-1'-piperazinyl]carbonyl]methyl]-1',2',4'-trioxaspiro[4.5]decane, 4-Oxoadamantane-2-spiro-3'-1',2',4'-trioxaspiro[4.5]decane, cis-Adamantane-2-spiro-3'-8'-[4'-(3'-aminopropoxy)phenyl]-1',2',4'-trioxaspiro[4.5]decane mesylate, and 6-Oxoadamantane-2-spiro-3'-1',2',4'-trioxaspiro[4.5]decane, and a pharmaceutically acceptable carrier.

5. Cis-Adamantane-2-spiro-3'-8'-[4'-(2'-aminoethoxy)phenyl]-1',2',4'-trioxaspiro[4.5]decane hydrochloride.

6. Cis-Adamantane-2-spiro-3'-8'-[4'-(2'-aminoethoxy)phenyl]-1',2',4'-trioxaspiro[4.5]decane maleate.

7. Cis-Adamantane-2-spiro-3'-8'-[4'-(2'-aminoethoxy)phenyl]-1',2',4'-trioxaspiro[4.5]decane citrate.

8. Cis-Adamantane-2-spiro-3'-8'-[[(3'-anino-3'-oxopropyl)amino]methyl]-1',2',4'-trioxaspiro[4.5]decane p-tosylate.

9. Cis-Adamantane-2-spiro-3'-8'-[4'-(3'-aminopropoxy)phenyl]-1',2',4'-trioxaspiro[4.5]decane mesylate.

10. A method of inhibiting malarial infection or treating malaria comprising: administrating an amount of a spiro or dispiro 1,2,4-trioxolane in a pharmaceutically acceptable carrier, said trioxolane being selected from the group consisting of cis-Adamantane-2-spiro-3'-8'-[2'-(1'H-tetrazol-5'-yl)ethyl]-1',2',4'-trioxaspiro[4.5]decane, Cis-Adamantane-2-spiro-3'-8'-[(1'-piperidinylsulfonyl)methyl]1',2',4'-trioxaspiro[4.5]decane, cis-Adamantane-2-spiro-3'-8'-[[1'-(2'-amino-2'-methylpropyl)-1'H-tetrazol-5'yl]methyl]-1',2',4'-trioxaspiro[4.5]decane, cis-Adamantane-2-spiro-3'-8'-[4'-hydroxy-3'-(methoxymethyl)phenyl]-1',2',4'-trioxaspiro[4.5]decane, cis-Adamantane-2-spiro-3'-8'-[4'-[2'-[(aminoiminomethyl)amino]ethoxy]phenyl]-1',2',4'-trioxaspiro[4.5]decane hydrochloride, cis-Adamantane-2-spiro-3'-8'-[4'-(2'-aminoethoxy)phenyl]-1',2',4'-trioxaspiro[4.5]decane hydrochloride, cis-Adamantane-2-spiro-3'-8'-[4'-(2'-aminoethoxy)phenyl]-1',2',4'-trioxaspiro[4.5]decane maleate, cis-Adamantane-2-spiro-3'-8'-[4'-(2'-aminoethoxy)phenyl]-1',2',4'-trioxaspiro[4.5]decane citrate, cis-Adamantane-2-spiro-3'-8'-carboxymethy-1',2',4'-trioxaspiro[4.5]decane sodium salt, trans, cis-5-Hydroxyadamantane-2-spiro-3'-8'-carboxymethyl-1',2',4'-trioxa-spiro[4.5]decane, trans, cis-5-Hydroxyadamantane-2-spiro-3'-8'-[[[(2'-amino-2'-methylpropyl)-amino]carbonyl]methyl]-1',2',4'-trioxaspiro[4.5]decane p-tosylate, cis-Adamantane-2-spiro-3'-8'-[4'-hydroxy-3'-(hydroxymethyl)phenyl]-1',2',4'-trioxaspiro[4.5]decane, cis-Adamantane-2-spiro-3'-8'-[3'-[(acetylamino)methyl]-4'-hydroxyphenyl]-1',2',4'-trioxaspiro[4.5]decane, cis-Adamantane-2-spiro-3'-8'-[[(3'-amino-3'-oxopropyyl)amino]methyl]-1',2',4'-trioxaspiro[4.5]decane p-tosylate, cis-Adamantane-2-spiro-3'-8'-[3'-(aminomethyl)-4'-hydroxyphenyl]-1',2',4'-trioxaspiro[4.5]decane p-tosylate, trans-Adamantane-2-spiro-3'-8'-hydroxymethyl-1',2',4'-trioxaspiro[4.5]decane, cis-Adamantane-2-spiro-3'-8'-formyl-1',2',4'-trioxaspiro[4.5]decane, Adamantane-2-spiro-3'-8',8'-bis(ethoxycarbonyl)-1',2',4'-trioxaspiro[4.5]de-cane, Adamantane-2-spiro-3'-8',8'-dicarboxy-1',2',4'-trioxaspiro[4.5]decane, Adamantane-2-spiro-3'-8',8'-bis(hydroxymethyl)-1',2',4'-trioxaspiro[4.5]de-cane, Adamantane-2-spiro-3'-7',7'-dimethyl-1',2',4'-trioxaspiro[4.5]decane, trans-Adamantane-2-spiro-3'-8'-[[[(2'-amino-2'-methylpropyl)amino]carbonyl]methyl]-1',2',4'-trioxaspiro[4.5]decane p-tosylate, cis, cis-5-Hydroxyadamantane-2-spiro-3'-8'-[[[(2'-amino-2'-methylpropyl)-amino]carbonyl]methyl]-1',2',4'-trioxaspiro[4.5]decane p-tosylate, cis-Adamantane-2-spiro-3'-8'-[2'-(methoxycarbonyl)ethyl]-1',2',4'-trioxaspiro[4.5]decane, cis-Adamantane-2-spiro-3'-8'-[[[4'-(2'-hydroxyethyl)-1'-piperazinyl]carbonyl]methyl]-1',2',4'-trioxaspiro[4.5]decane, 4-Oxoadamantane-2-spiro-3'-1',2',4'-trioxaspiro[4.5]decane, cis-Adamantane-2-spiro-3'-8'-[4'-(3'-aminopropoxy)phenyl]-1',2',4'-trioxaspiro[4.5]decane mesylate, cis-Adamantane-2-spiro-3'-8'-[4'-(3'-aminopropoxy)phenyl]-1',2',4'-trioxaspiro[4.5]decane mesylate and 6-Oxoadamantane-2-spiro-3'-1',2',4'-trioxaspiro[4.5]decane.

11. A method of inhibiting schistosomiasis infection or treating schistosomiasis comprising: administering an mount of a spiro or dispiro 1,2,4-trioxolane effective in inhibiting schistosomiasis infection or effective for treating schistosomiasis, said trioxolane in a pharmaceutically acceptable carrier, and further providing that said trioxolane is selected from the group consisting of: cis-Adamantane-2-spiro-3'-8'-[2'-(1'H-tetrazol-5'-yl)ethyl]-1',2',4'-trioxaspiro[4.5]decane, cis-Adamantane-2-spiro-3'-8'-[(1'-piperidinyl-sufonyl)methyl]-1',2',4'-trioxaspiro[4.5]decane, cis-Adamantane-2-spiro-3'-8'-[[1'-(2'-amino-2'-methylpropyl)-1'H-tetrazol5'-yl]methyl]-1',2',4'-trioxaspiro[4.5]decane, cis-Adamantane-2-spiro-3'-8'-[4'-hydroxy-3'-(methoxymethyl)phenyl]-1',2',4'-trioxaspiro[4.5]decane, cis-Adamantane-2-spiro-3'-8'-[4'-[2'-[(aminoiminomethyl)amino]ethoxy]phenyl]-1',2',4'-trioxaspiro[4.5]decane hydrochloride, cis-Adamantane-2-spiro-3'-8'-[4'-(2'-aminoethoxy)phenyl]-1',2',4'-trioxaspiro[4.5]decane hydrochloride, cis-Adamantane-2-spiro-3'-8'-[4'-(2'-aminoethoxy)phenyl]-1',2',4'-trioxyspiro[4.5]decane maleate, cis-Adamantane-2-spiro-3'-8'-[4'-(2'-aminoethoxy)phenyl]-1',2',4'-trioxaspiro[4.5]decane citrate, cis-Adamantane-2-spiro-3'-8'-carboxymethy-1',2',4'-trioxaspiro[4.5]decane sodium salt, trans, cis-5-Hydroxyadamantane-2-spiro-3'-8'-carboxymethyl-1',2',4'-trioxa-spiro[4.5]decane, trans, cis-5-Hydroxyadamantane-2-spiro-3'-8'-[[[(2'-amino-2'-methylpropyl)-amino]carbonyl]methyl]-1',2',4'-trioxaspiro[4.5]decane p-tosylate, cis-Adamantane-2-spiro-3'-8'-[4'-hydroxy-3'-(hydroxymethyl)phenyl]-1',2',4'-trioxaspiro[4.5]decane, cis-Adamantane-2-spiro-3'-8'-[3'-[(acetylamino)methyl]-4'-hydroxyphenyl]-1',2',4'-trioxaspiro[4.5]decane, cis-Adamantane-2-spiro-3'-8'-[[(3'-amino-3'-oxopropyyl)amino]methyl]-1',2',4'-trioxaspiro[4.5]decane p-tosylate, cis-Adamantane-2-spiro-3'-8'-[3'-(aminomethyl)-4'-hydroxyphenyl]-1',2',4'-trioxaspiro[4.5]decane p-tosylate, trans-Adamantane-2-spiro-3'-8'-hydroxymethyl-1',2',4'-trioxaspiro[4.5]decane, cis-Adamantane-2-spiro-3'-8'-formyl-1',2',4'-trioxaspiro[4.5]decane, Adamantane-2-spiro-3'-8',8'-bis(ethoxycarbonyl)-1',2',4'-trioxaspiro[4.5]de-cane, Adamantane-2-spiro-3'-8',8'-dicarboxy-1',2',4'-trioxaspiro[4.5]decane, Adamantane-2-spiro-3'-8',8'-bis(hydroxymethyl)-1',2',4'-trioxyspiro[4.5]de-cane, Adamantane-2-spiro- 3'-7',7'-dimethyl-1',2',4'-trioxaspiro[4.5]decane, trans-Adamantane-2-spiro-3'-8'-[[[(2'-amino-2'-methylpropyl)amino]carbonyl]methyl]-1',2',4'-trioxaspiro[4.5]decane p-tosylate, cis, cis-5-Hydroxyadamantane-2-spiro-3'-8'-[[[(2'-amino-2'-methylpropyl)amino]carbonyl]methyl]-1',2',4'-trioxaspiro[4.5]decane p-tosylate, cis-Adamantane-2-spiro-3'-8'-[2'-(methoxycarbonyl)ethyl]-1',2',4'-trioxaspiro[4.5]decane, cis-Adamantane-2-spiro-3'-8'-[[[4'-(2'-hydroxyethyl)-1'-piperazinyl]carbonyl]methyl]-1',2',4'-trioxaspiro[4.5]decane, 4-Oxoadamantane-2-spiro-3'-1',2',4'-trioxaspiro[4.5]decane, cis-Adamantane-2-spiro-3'-8'-[4'-(3'-aminopropoxy)phenyl]-1',2',4'-trioxaspiro[4.5]decane mesylate, cis-Adamantane-2-spiro-3'-8'-[4'-(3'-aminopropoxy)phenyl]-1',2',4'-trioxaspiro[4.5]decane mesylate and 6-Oxoadamantane-2-spiro-3'-1',2',4'-trioxaspiro[4.5]decane.

\* \* \* \* \*

UNITED STATES PATENT AND TRADEMARK OFFICE
CERTIFICATE OF CORRECTION

PATENT NO. : 7,371,778 B2  Page 1 of 1
APPLICATION NO. : 11/121451
DATED : May 13, 2008
INVENTOR(S) : Vennerstrom et al.

It is certified that error appears in the above-identified patent and that said Letters Patent is hereby corrected as shown below:

Title Page, item (75) Inventors, 7<sup>th</sup> line:
DELETE:
   William N. "Chapman" and insert
   William N. --Charman--

Signed and Sealed this

Second Day of September, 2008

JON W. DUDAS
*Director of the United States Patent and Trademark Office*